[19] United States Patent
Bedenbaugh

(10) Patent No.: US 9,162,049 B2
(45) Date of Patent: *Oct. 20, 2015

(54) DEVICES AND METHODS FOR TISSUE MODULATION AND MONITORING

(71) Applicant: Boston Scientific Neuromodulation Corporation, Valencia, CA (US)

(72) Inventor: Purvis Bedenbaugh, Tampa, FL (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/049,072

(22) Filed: Oct. 8, 2013

(65) Prior Publication Data
US 2014/0088672 A1   Mar. 27, 2014

Related U.S. Application Data

(63) Continuation of application No. 12/880,985, filed on Sep. 13, 2010, now Pat. No. 8,583,237.

(51) Int. Cl.
*A61N 1/00* (2006.01)
*A61N 1/05* (2006.01)
(Continued)

(52) U.S. Cl.
CPC ............ *A61N 1/0529* (2013.01); *A61B 5/0478* (2013.01); *A61N 1/0534* (2013.01);
(Continued)

(58) Field of Classification Search
CPC ............ A61N 1/00; A61N 1/02; A61N 1/04; A61N 1/0472; A61N 1/0476; A61N 1/048; A61N 1/0488; A61N 1/36; A61N 1/3605; A61N 1/36125; A61N 1/372
See application file for complete search history.

(56) References Cited

U.S. PATENT DOCUMENTS 4,044,774 A   8/1977   Corbin et al.
4,602,624 A   7/1986   Naples et al.
(Continued)

FOREIGN PATENT DOCUMENTS

EP   0580928 A1   2/1994
EP   0650694 B1   7/1998
(Continued)

OTHER PUBLICATIONS

Official Communication for U.S. Appl. No. 11/828,547 mailed May 14, 2009.
(Continued)

*Primary Examiner* — Christopher D Koharski
*Assistant Examiner* — Elizabeth K So
(74) *Attorney, Agent, or Firm* — Lowe Graham Jones PLLC; Bruce E. Black

(57) ABSTRACT

A tissue stimulating device has an elongate member, a proximal annular stimulating region and a distal annular stimulating region. Each of the annular stimulating regions circumscribe the elongate member, and each has a plurality of independently energizable electrodes that deliver current into tissue. Adjacent electrodes in the annular stimulating regions are separated from one another by an insulating member. The annular stimulating regions are axially separated from one another by a gap. An internal electrical connector electrically couples a first electrode in the proximal annular stimulating region with a first electrode in the distal annular stimulating region. The first internal electrical connector is disposed within the elongate member, and extends across the gap between annular stimulating regions. A recording electrode is disposed in the gap and is adapted to record local tissue potentials from the tissue.

20 Claims, 26 Drawing Sheets

(51) Int. Cl.
*A61B 5/0478* (2006.01)
*A61N 1/36* (2006.01)

(52) U.S. Cl.
CPC ......... *A61N1/36182* (2013.01); *A61N 1/36067* (2013.01); *A61N 1/36082* (2013.01); *A61N 1/36185* (2013.01)

(56) References Cited

U.S. PATENT DOCUMENTS

| | | |
|---|---|---|
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |
| 5,374,285 A | 12/1994 | Vaiani et al. |
| 5,405,375 A | 4/1995 | Ayers et al. |
| 5,458,629 A | 10/1995 | Baudino et al. |
| 5,522,874 A | 6/1996 | Gates |
| 5,683,422 A | 11/1997 | Rise |
| 5,711,316 A | 1/1998 | Elsberry et al. |
| 5,713,922 A | 2/1998 | King |
| 5,716,377 A | 2/1998 | Rise et al. |
| 5,800,350 A | 9/1998 | Coppleson et al. |
| 5,843,148 A | 12/1998 | Gijsbers et al. |
| 5,891,084 A | 4/1999 | Lee |
| 5,938,688 A | 8/1999 | Schiff |
| 5,987,361 A | 11/1999 | Mortimer |
| 6,011,996 A | 1/2000 | Gielen et al. |
| 6,018,684 A | 1/2000 | Bartig et al. |
| 6,038,480 A | 3/2000 | Hrdlicka et al. |
| 6,094,598 A | 7/2000 | Elsberry et al. |
| 6,134,478 A | 10/2000 | Spehr |
| 6,161,047 A | 12/2000 | King et al. |
| 6,167,311 A | 12/2000 | Rezai |
| 6,227,203 B1 | 5/2001 | Rise et al. |
| 6,301,492 B1 | 10/2001 | Zonenshayn |
| 6,322,559 B1 | 11/2001 | Daulton et al. |
| 6,475,750 B1 | 11/2002 | Han et al. |
| 6,484,057 B2 | 11/2002 | Ideker et al. |
| 6,510,347 B2 | 1/2003 | Borkan |
| 6,529,774 B1 | 3/2003 | Greene |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 6,997,922 B2 | 2/2006 | Theeuwes et al. |
| 7,006,872 B2 | 2/2006 | Gielen et al. |
| 7,010,356 B2 | 3/2006 | Jog et al. |
| 7,027,852 B2 | 4/2006 | Helland |
| 7,047,082 B1 | 5/2006 | Schrom et al. |
| 7,047,084 B2 | 5/2006 | Erickson et al. |
| 7,051,419 B2 | 5/2006 | Schrom et al. |
| 7,146,222 B2 | 12/2006 | Boling |
| 7,174,213 B2 | 2/2007 | Pless |
| 7,181,288 B1 | 2/2007 | Rezai et al. |
| 7,203,548 B2 | 4/2007 | Whitehurst et al. |
| 7,292,890 B2 | 11/2007 | Whitehurst et al. |
| 7,305,268 B2 | 12/2007 | Gliner et al. |
| 7,337,005 B2 | 2/2008 | Kim et al. |
| 7,346,382 B2 | 3/2008 | McIntyre et al. |
| 7,489,971 B1 | 2/2009 | Franz |
| 7,617,006 B2 | 11/2009 | Metzler et al. |
| 7,668,601 B2 | 2/2010 | Hegland et al. |
| 7,676,273 B2 | 3/2010 | Goetz et al. |
| 7,761,985 B2 | 7/2010 | Hegland et al. |
| 7,822,482 B2 | 10/2010 | Gerber |
| 7,840,188 B2 | 11/2010 | Kurokawa |
| 7,848,802 B2 | 12/2010 | Goetz et al. |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,583,237 B2 | 11/2013 | Bedenbaugh |
| 2001/0023368 A1 | 9/2001 | Black et al. |
| 2002/0062143 A1 | 5/2002 | Baudino et al. |
| 2002/0156513 A1 | 10/2002 | Borkan |
| 2002/0183817 A1 | 12/2002 | Van Venrooij et al. |
| 2003/0195602 A1 | 10/2003 | Boling |
| 2004/0015205 A1 | 1/2004 | Whitehurst et al. |
| 2004/0039434 A1 | 2/2004 | Schrom et al. |
| 2004/0267328 A1 | 12/2004 | Duffin et al. |
| 2005/0015130 A1 | 1/2005 | Gill |
| 2005/0038489 A1 | 2/2005 | Grill |
| 2005/0171587 A1 | 8/2005 | Daglow et al. |
| 2005/0222642 A1 | 10/2005 | Przybyszewski et al. |
| 2005/0246004 A1 | 11/2005 | Cameron et al. |
| 2005/0246006 A1 | 11/2005 | Daniels |
| 2006/0004422 A1 | 1/2006 | De Ridder |
| 2006/0025841 A1 | 2/2006 | McIntyre |
| 2006/0041284 A1 | 2/2006 | Cameron et al. |
| 2006/0047325 A1 | 3/2006 | Thimineur et al. |
| 2006/0247697 A1 | 11/2006 | Sharma et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2007/0225674 A1 | 9/2007 | Molnar et al. |
| 2007/0255373 A1 | 11/2007 | Metzler et al. |
| 2008/0004674 A1 | 1/2008 | King et al. |
| 2008/0004675 A1 | 1/2008 | King et al. |
| 2008/0027504 A1 * | 1/2008 | Bedenbaugh ................... 607/45 |
| 2008/0046036 A1 | 2/2008 | King et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0204192 A1 | 8/2009 | Carlton et al. |
| 2009/0204193 A1 | 8/2009 | Kokones et al. |
| 2010/0023089 A1 | 1/2010 | DiLorenzo |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |

(56) References Cited

U.S. PATENT DOCUMENTS

| | | | |
|---|---|---|---|
| 2013/0261684 A1 | 10/2013 | Howard | |
| 2013/0317587 A1 | 11/2013 | Barker | |
| 2013/0325091 A1 | 12/2013 | Pianca et al. | |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | WO-9732628 A1 | 9/1997 |
| WO | WO-9955411 A3 | 2/2000 |
| WO | WO-0038574 A1 | 7/2000 |
| WO | 0158520 A1 | 8/2001 |
| WO | WO-02/68042 A1 | 9/2002 |
| WO | WO-2004045707 A1 | 6/2004 |
| WO | 2008018067 A2 | 2/2008 |
| WO | WO-2008053789 A1 | 5/2008 |
| WO | 2008/100841 A1 | 8/2008 |
| WO | WO-2009025816 A1 | 2/2009 |
| WO | WO-2009102536 A1 | 8/2009 |
| WO | 2013162775 A2 | 10/2013 |
| WO | 2014018092 A1 | 1/2014 |

OTHER PUBLICATIONS

Seigel, "Hard/Soft Microfabrication for Biosensing and Drug Delivery," University of Minnesota Nanotechnology Presentation, 9 pages total. Downloaded from http://www.business.umn.edu/documents/RonSeigel.pdf.

Steege et al., "Assessment of a New Prototype Hydrogel CO2 Sensor; Comparison with Air Tonometry," The Journal of Clinical Monitoring and Computing, vol. 21, No. 2, 2007, pp. 83-90.

U.S. Appl. No. 13/951,057, filed Jul. 25, 2013.

U.S. Appl. No. 14/053,112, filed Oct. 14, 2013.

U.S. Appl. No. 12/880,985 Official Communication mailed Sep. 28, 2012.

International Search Report and Written Opinion for International Patent Application No. PCT/US2011/050420 dated Dec. 23, 2011.

U.S. Appl. No. 13/665,533, Official Communication mailed Jun. 13, 2013.

Official Communication for U.S. Appl. No. 13/665,553 mailed Jun. 24, 2014.

Official Communication for U.S. Appl. No. 13/665,533 mailed Jan. 23, 2014.

U.S. Appl. No. 14/286,940, filed May 23, 2014.

U.S. Appl. No. 14/286,889, filed May 23, 2014.

U.S. Appl. No. 14/286,934, filed May 23, 2014.

U.S. Appl. No. 14/325,249, filed Jul. 7, 2014.

U.S. Appl. No. 14/332,212, filed Jul. 15, 2014.

U.S. Appl. No. 14/452,461, filed Aug. 5, 2014.

U.S. Appl. No. 14/286,829, filed May 23, 2014.

U.S. Appl. No. 14/469,214, filed Aug. 26, 2014.

U.S. Appl. No. 14/286,797, filed May 23, 2014.

Baldi et al., "A Hydrogel-Actuated Environmentally Sensitive Microvalve for Active Flow Control," Journal of Microelectromechanical Systems, vol. 12, No. 5, 2003, pp. 613-621.

Baldi et al., "A Microstructure Silicon Membrane with Entrapped Hydrogels for Environmentally Sensitive Fluid Gating," Sensor and Actuators B, No. 114, vol. 1, 2006, pp. 9-18.

Bashir et al., "Micromechanical Cantilever as an Ultrasensitive pH Microsensor," Applied Physics Letters, vol. 81, No. 16, 2002, pp. 3091-3093.

Cheung et al., "Tinnitus modulation by deep brain stimulation in locus of caudate neurons (area LC)," Neuroscuience, vol. 169, No. 4, Sep. 15, 2010, pp. 1768-1778.

European Search Report and Search Opinion for European Patent No. 07799919.1 dated Nov. 30, 2009.

International Search Report and Written Opinion for International Patent Application No. PCT/US2007/074746 dated Aug. 15, 2008.

Krsko et al., "Biointeractive Hydrogels," Materials Today, vol. 8, No. 12, Dec. 2005, pp. 36-44.

Official Communication for U.S. Appl. No. 11/828,547 mailed Aug. 6, 2008.

Official Communication for U.S. Appl. No. 11/828,547 mailed Dec. 8, 2009.

Official Communication for U.S. Appl. No. 11/828,547 mailed Jan. 9, 2009.

U.S. Appl. No. 14/557,211, filed Dec. 1, 2014.

* cited by examiner

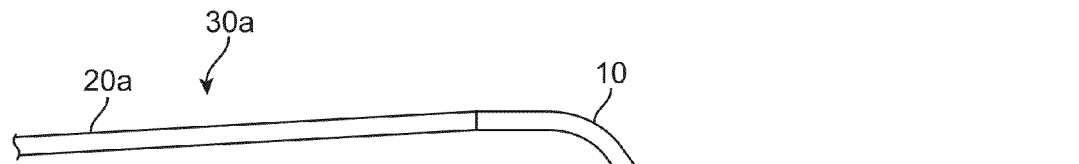
FIG. 1
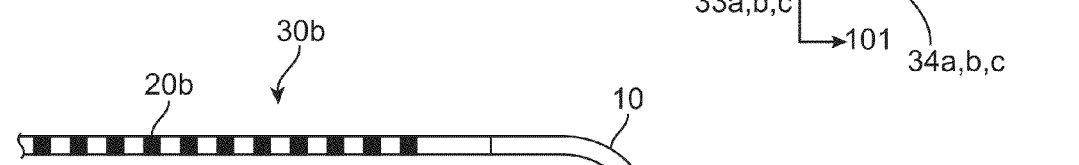
FIG. 2
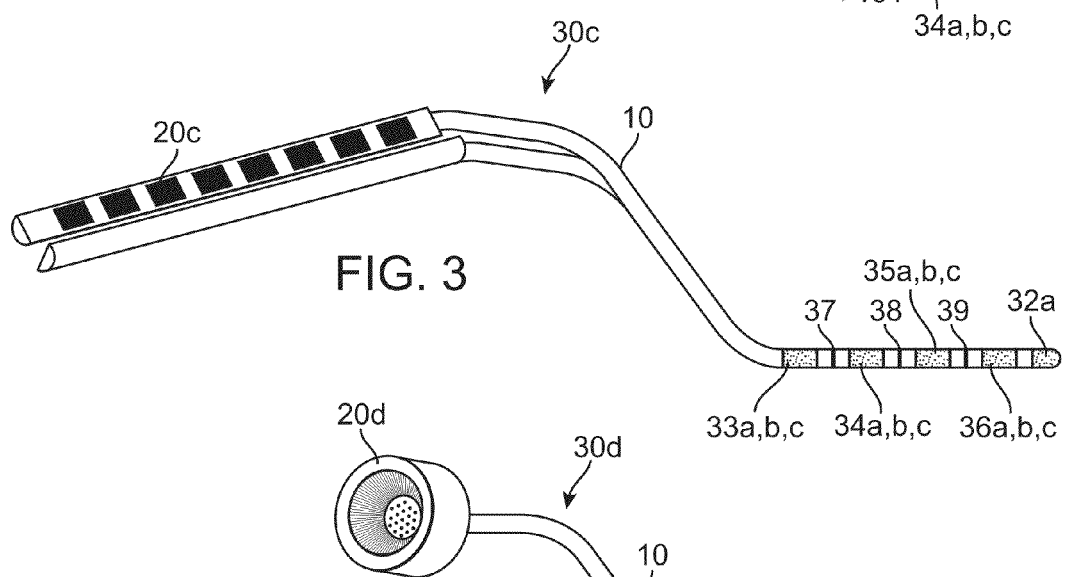
FIG. 3
FIG. 4

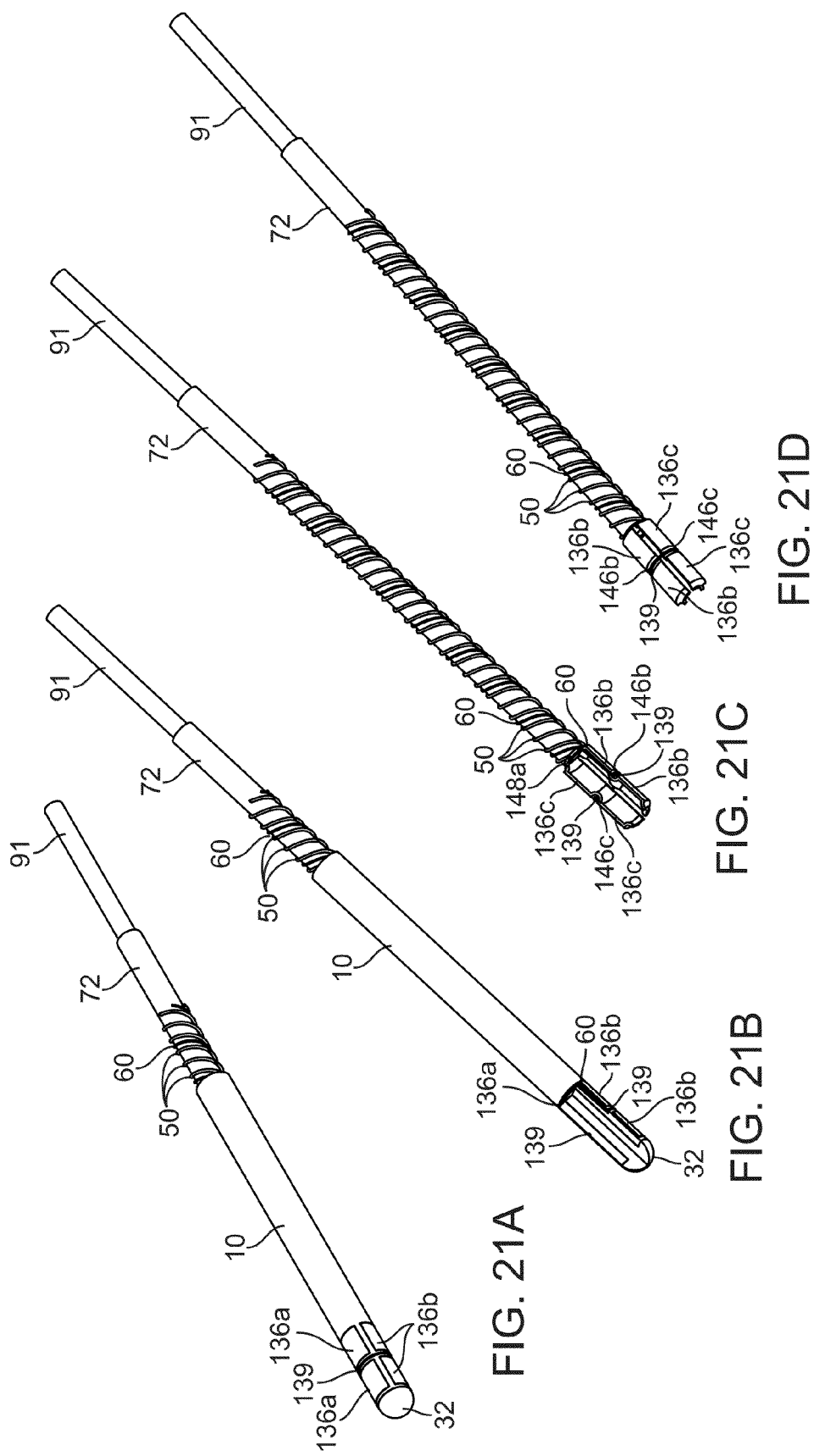

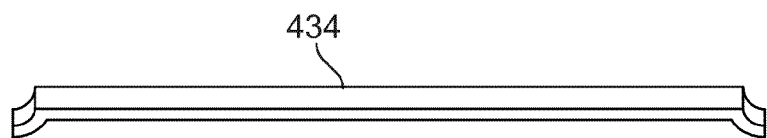
FIG. 28A
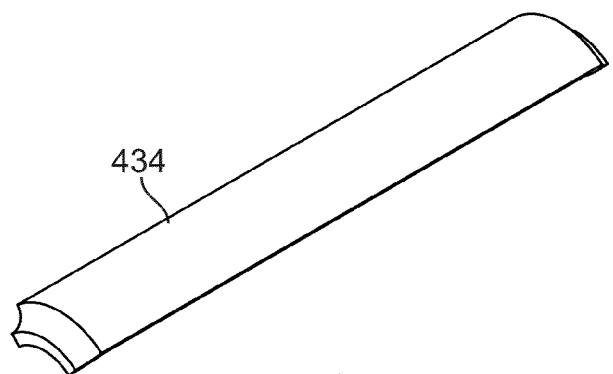
FIG. 28B
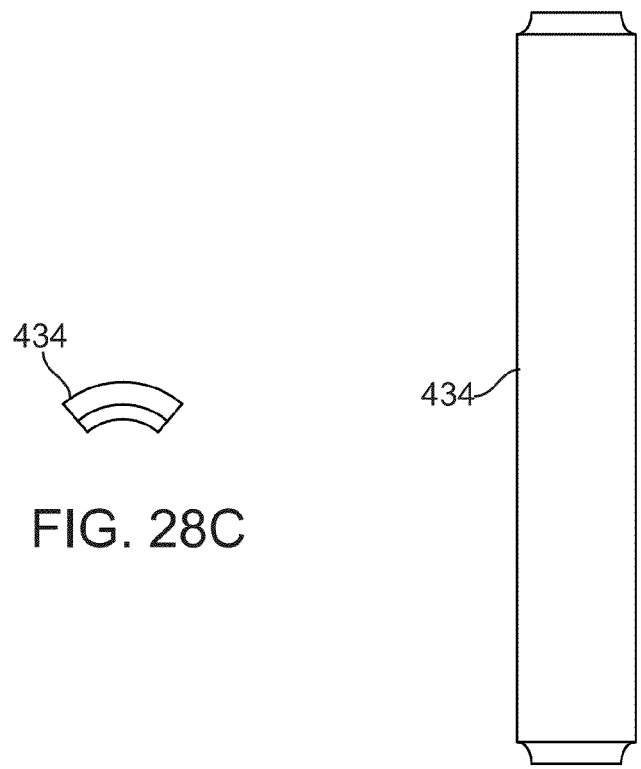
FIG. 28C
FIG. 28D

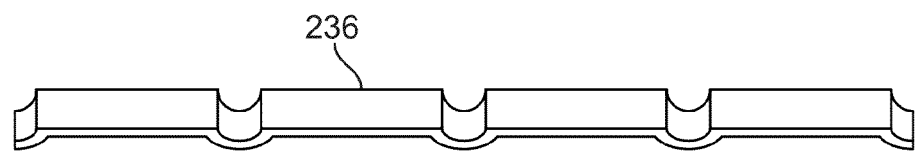
FIG. 31A
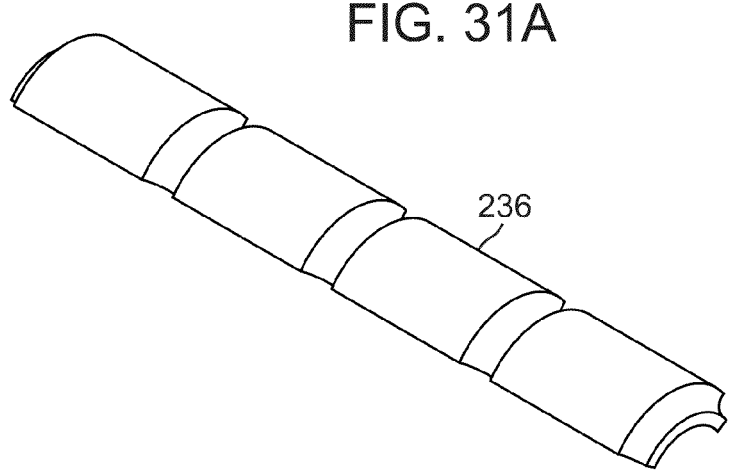
FIG. 31B
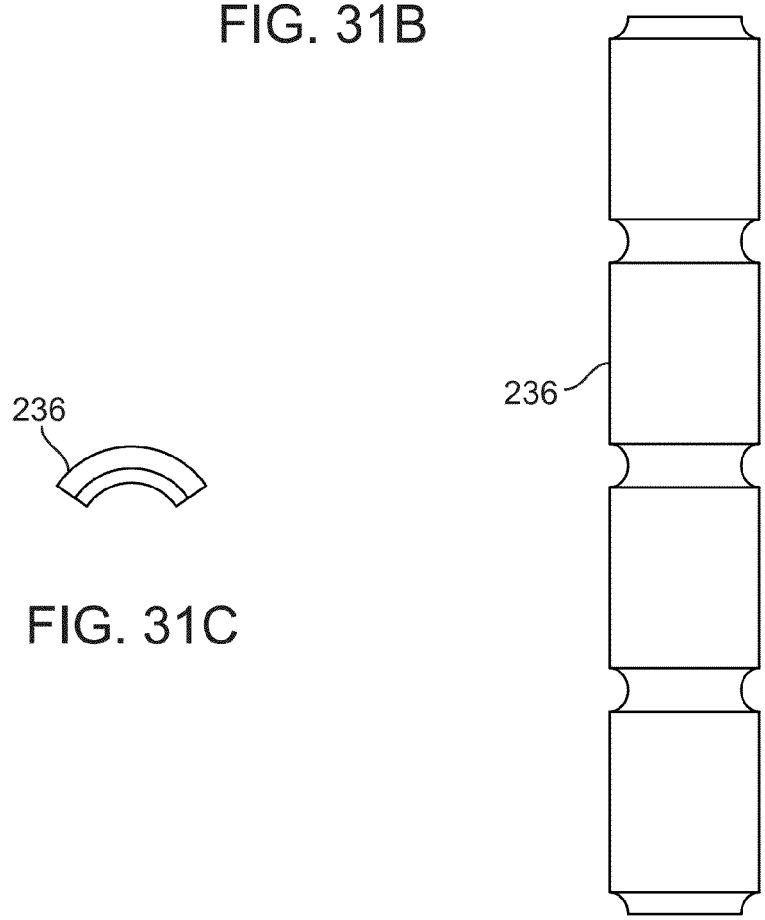
FIG. 31C
FIG. 31D

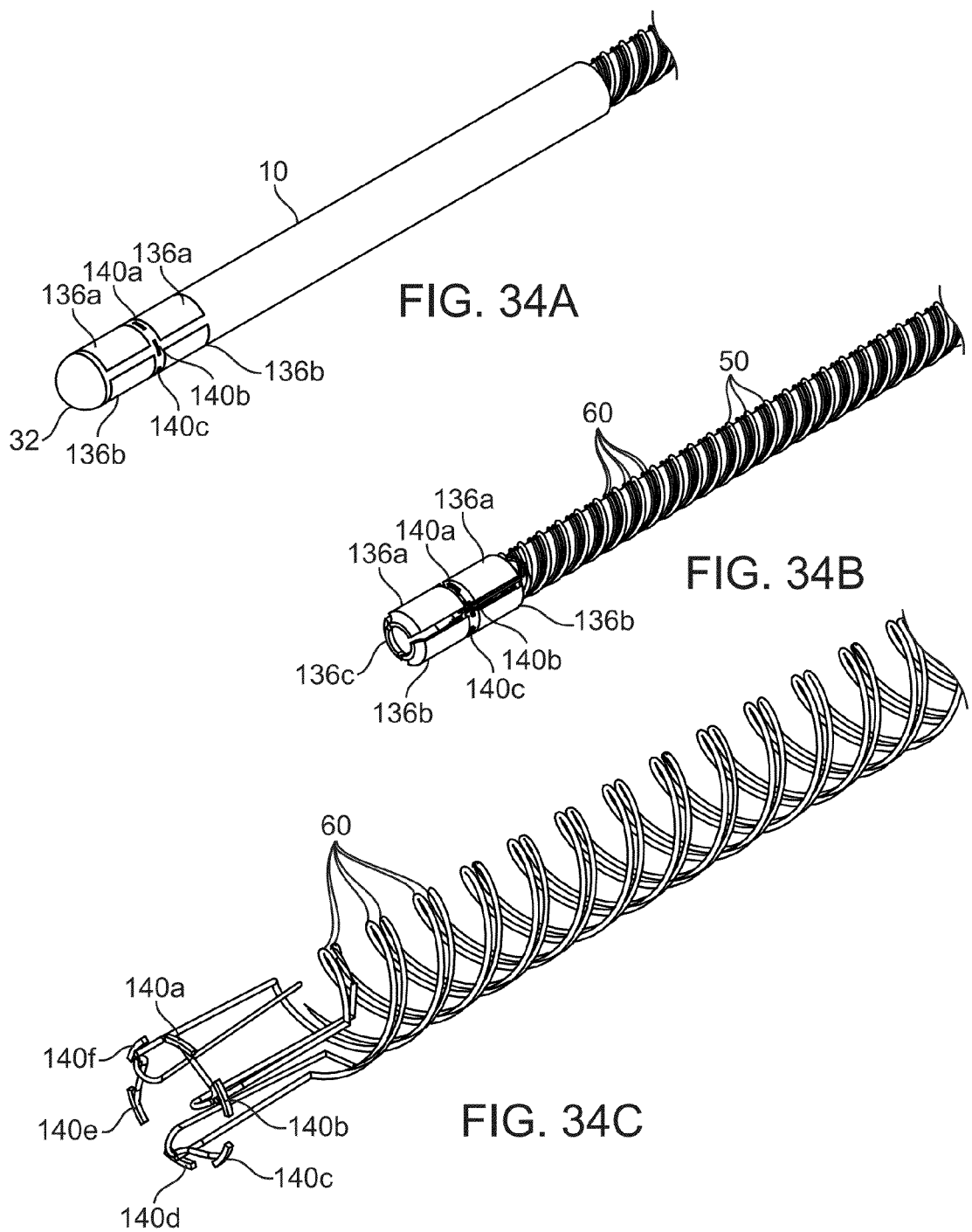

DEVICES AND METHODS FOR TISSUE MODULATION AND MONITORING

CROSS-REFERENCE

The present application is a continuation of U.S. patent application Ser. No. 12/880,985, now U.S. Pat. No. 8,583,237, filed Sep. 13, 2010.

The present application is related to U.S. patent application Ser. No. 11/828,547, now U.S. Pat. No. 8,321,025, filed Jul. 26, 2007, the full disclosure of which is incorporated herein by reference.

BACKGROUND OF THE INVENTION

1. Field of the Invention

This invention relates generally to medical apparatus and methods, and more specifically to leads used to electrically and/or chemically modulate and monitor tissues of the brain.

Implanting medical devices such as probes or leads within the cranium is an increasingly important approach for treatment of diseases such as Parkinson's disease, essential tremor and dystonia. Implants may be used to treat a wide array of disorders, such as depression, epilepsy, dystonia, obsessive compulsive disorder, obesity, chronic pain, tinnitus, and phantom perceptions. Most of these devices interact with the brain by applying current through an electrode. In addition, infusion of drugs through a chronically implanted lead has been proposed in the medical literature either as a primary treatment, or as an adjunctive treatment to electrical stimulation, in patients with Alzheimer's and Parkinson's diseases, among others.

Existing implantable probes are typically configured as small diameter cylinders or tubes, with several circumferential metal rings near the distal tip, and an electrically passive central axial lumen. The metal rings are used to provide electrical stimulation, while the central axial lumen can be used to deliver the probe over a guidewire or stylet during the implantation procedure.

In most treatment protocols, a sequence of electrical pulses is applied to one or more conducting rings on the probe. Typically monopolar or bipolar stimulation of the conducting rings is used. In monopolar stimulation, a single circumferential ring is stimulated with a charge balanced biphasic electrical pulse, with a return path for the current at a remote site, such as a battery pack or control module. In bipolar stimulation, a combination of rings are stimulated with charge balanced biphasic electrical pulses of opposite polarity. Stimulation of the conducting rings produces a field of action which is more or less symmetric about the probe, with some asymmetries arising because of anisotropy in the electrical properties of the adjacent neural or brain tissue.

Choosing an electrode or group of electrodes to energize, and differentially regulating the current through members of a group of electrodes, are methods for refining the effects of modulating a target tissue with electrical stimulation.

A symmetrical electrical field about the probe axis is not always desirable. For example, when the probe is not implanted at the center of the modulation target or when the brain target is asymmetric or irregular in shape. Additionally, there are often neuronal domains near the targeted zone which should not be modulated. Modulating non-target zones can lead to undesirable side effects, including somatic sensation, involuntary movement and impaired vision, among others.

It is desirable to not only modulate brain activity, but also to monitor it along with physiological and pathophysiological states. Monitoring obtains information on neuronal activity near the stimulation sites, including field potentials and extracellularly recorded action potentials. Such potentials may be observed on an ongoing basis, in the course of electrical stimulation for treatment, and in the course of special stimulation and response experiments designed to assess an individual's brain and the brain to electrode interface. Information obtained from monitoring at intervals may be used to control and adjust treatment on an ongoing, day-to-day basis by a patient, or in follow up visits to a health professional. Information obtained from monitoring may also be used to dynamically adjust the treatment by an automated control system or control algorithm, and by updating the parameters of a controller.

Monitoring at intervals can be used to track changes in the brain response to stimulation as a function of stimulus magnitude. Clinical decisions can be based upon estimated parameters, such as the threshold stimulus level which barely generates a response, and the stimulus level which just saturates the observed response. The shape of the stimulus response function, for example whether it is concave up, concave down, or linear, may also provide information relevant for adjusting treatment. The dynamic range from threshold to saturation measured near the stimulation site may directly correspond to the dynamic range of clinical effect, or it may be correlated with it. In either case, the locally measured dynamic range gives information which can accelerate the initial fitting and guide ongoing adjustments in treatment protocol. Brain plasticity in response to treatment may be tracked by changes in the dynamic range.

Consider the application of monitoring at intervals to the treatment of Parkinson's disease. It is well known that the beneficial effects of electrical stimulation to Parkinson's patients do not appear for several minutes or hours after the stimulation protocol is initiated. If the protocol is discontinued during sleep and resumed at waking, the beneficial effects of treatment may not appear again for many hours. Monitoring at intervals offers the opportunity to track changes in the response to stimulation, so that stimulation can be applied during one protocol in order to bring about the beneficial effects, and under another more conservative protocol in order to just maintain the beneficial effects. Such a strategy would conserve battery power, and could also reduce side effects.

By monitoring from moment to moment, a modulatory treatment can be dynamically synchronized with natural brain rhythms upon an observed pathological or normal physiological state, or controlled by an automatic control system or control algorithm.

Most procedures currently performed monitor patient motions, behaviors, or brain activity at a site remote from the site of an electrically stimulating probe, and this information is used to adjust brain stimulation parameters. Parameters are adjusted on a short time scale, to generate a desired effect and minimize side effects, and on a longer time scale, to account for brain plasticity. Brain plasticity is due to an adaptive response by the brain to an intervention and it is well known that ongoing responses by the brain to an intervention such as modulating therapy often differ from the initial response. Useful information may also be obtained by monitoring electrical potentials near the site of electrical stimulation and therefore it would be desirable to monitor brain activity at the locus of electrical stimulation. Monitoring allows the course of the disease and healing processes to be evaluated along with the prognosis for various treatment options.

For these reasons as well as others, it would be desirable to provide improved probes for modulating and monitoring tissues such as the brain. It would be particularly desirable to provide an efficient design for generating a directed electrical field that may be steered towards the intended target, and/or away from other brain areas. It is also desirable to provide a probe with an efficient number and size of electrodes as well as connector leads that integrates both electrical recording and stimulating or modulating capabilities, where the information from recordings is obtained close to the treatment site and can be used to define the stimulating protocol. The protocol can then be adapted either statically or dynamically and as the disease state changes, the therapy can also be adjusted. Recording and monitoring of brain electrical activity is also used to determine when the stimulation protocol is applied or whether it should be reserved for times when it is more effective, thereby helping to conserve power. At least some of these objectives will be met by the inventions described hereinbelow.

2. Description of the Background Art

Prior patents and publications describing brain modulating probes and methods include: U.S. Publication Nos. 2006/0047325; 2006/0004422; 2005/0015130; 2004/0039434 and U.S. Pat. Nos. 7,051,419; 7,047,082; 7,006,872; 6,094,598; 6,038,480; 6,011,996; 6,980,863; 5,843,148; and 5,716,377. U.S. Publication number 2004/026738 describes an electrical connector a multiple channel pacemaker lead.

Other related scientific literature include: A. A. Gorgulho, D. C. Shields, D. Malkasian, Eric Behnke, and Antonio A. F. DeSalles, "Stereotactic coordinates associated with facial musculature contraction during high-frequency stimulation of the subthalamic nucleus," Journal of Neurosurgery 110: 1317-1321, 2009; D. C. Shields, A. Gorgulho, E. Behnke, D. Malkasian, and A. F. Desalles, "Contralateral conjugate eye deviation during deep brain stimulation of the subthalamic nucleus," Neurosurgery 107:37-42, 2007; P. Sauleau, S. Raoul, F. Lallement, I. Rivier, S. Drapier, Y. Lajat, and M. Verin, "Motor and non motor effects during intraoperative subthalamic stimulation for Parkinson's disease." Neurology 252:457-464, 2005; E. H. Yeterian, D. N. Pandya, "Corticostriatal connections of the superior temporal region in rhesus monkeys," Journal of Comparative Neurology 399:384-402, 1998; E. H. Yeterian, D. N. Pandya, "Corticostriatal connections of extrastriate visual areas in rhesus monkeys," Journal of Comparative Neurology, 352:436-457, 1995; E. H. Yeterian, D. N. Pandya, "Prefrontostriatal connections in relation to cortical architectonic organization in rhesus monkeys," Journal of Comparative Neurology 312:43-67, 1991; and S. W. Cheung, P. S. Larson, "Tinnitus modulation by deep brain stimulation in locus of caudate neurons (area LC)," Neuroscience 169:1768-1778, 2010.

SUMMARY OF THE INVENTION

Embodiments of the invention generally provide an implantable probe or lead capable of modulating or stimulating tissue and measuring and recording local tissue responses as a result of the modulation. The terms "modulating" and "stimulating" are used interchangeably in order to refer to providing a stimulus that incites or suppresses activity in the tissue. The terms "probe" and "lead" are also used interchangeably in order to refer to any device that may be used to modulate the tissue and/or measure and record local tissue responses. Modulation of the tissue may include electrical and/or chemical stimulation of the tissue, as well as suppression of tissue activity. Measuring and recording tissue responses often entails measuring local tissue potentials in response to the stimulation but could also include measuring and recording endogenous tissue potentials as well as chemical activity in the tissue. Often, the probe is used in tissues of the brain, typically being implanted into deep brain structures, or into the cerebrum or cerebellum.

Embodiments of the invention also provide methods where therapeutic modulation may be directed within tissues such as neural structures with improved effectiveness and minimal undesirable side effects. Exemplary embodiments also include methods to electrically and/or chemically monitor tissue activity so that the therapeutic intervention may be modified to improve its effectiveness, or to conserve limited resources such as reagents or electrical charge.

Many embodiments of the lead possess electrodes for stimulating tissue such as the brain, and/or for recording tissue activity by measuring local tissue potentials. The stimulating electrodes are arranged so that they can be activated individually, or in combination. They may alternatively be activated in simultaneous or sequential coordination in order to shape the volume of stimulated brain tissue and regulate the magnitude and timing of activity in a stimulated brain. The probe often has a plurality of annular shaped stimulating regions disposed axially along the probe. An annular stimulating region may have one or more electrodes. For the most efficient use of the probe, each annular shaped electrode has three independent stimulation sites disposed thereon, although a greater number of stimulation sites per annular region may be employed. By "three independent stimulation sites," it is meant that the electrode is separable into three regions in communication with tissue or a body fluid, isolated from each other on the communicating surface of the probe by electrical insulation, typically disposed in approximately 120.degree. arcs of the annular electrode, where each region may be independently energized. In a related arrangement, electrodes within two or more regions may be internally electrically connected, so that they are always energized concurrently. The energizing charge may be transmitted along wires coursing from a proximal end of the probe to a distal end, may be coupled or transmitted wirelessly, may be obtained from a battery or fuel cell integrated with the probe, or may be obtained from another energy source.

Embodiments of the invention can be structured to achieve one or more efficiencies. Efficiency means to obtain a practical advantage while consuming a limited amount of constrained resources. Examples of constrained resources are the volume of target tissue which may be modulated to achieve a therapeutic effect, the surface area of a medical lead and modulating surfaces or devices fixedly attached to the lead, the electrical power which may be supplied to an implantable medical device, and the magnitude of the current which may be passed across an electrode-to-tissue interface without raising the risk of untoward side effects beyond an acceptable level given the context of a patient's age, disease process and the therapeutic benefit supplied through the action of the device. Further examples of constrained resources related to a deep brain stimulation and monitoring system comprised of a medical lead, lead extension, and controller or pulse generator, are the number of conductive channels in the overall conductive pathway, the number of conductive channels in electrical connectors between components of a deep brain stimulation and monitoring system, the number of sources of stimulating energy, and the number of recording amplifiers. Devices which address the number of channels in the connector of a medical lead as a limiting resource have been reported in the patent and scientific literature.

Embodiments of the invention may be specialized for modulating particular target tissues, or ensembles of target tissues. Structure which may be specialized for a particular target, such a locus of neurons in the caudate nucleus, the modulation of which can modulate tinnitus or the perception of tinnitus. The structure may be specialized so that modulating surfaces have an axial dimension related to the dimension of the target tissue, and so that current may be steered into the target tissue preferentially, and away from tissues the modulation of which could lead to side effects. Embodiments of the invention specialized for a particular target tissue may also include stimulating regions fixedly attached to the lead, with four electrodes in a region, the electrodes and interposed insulating surfaces together circumscribing the lead.

In a first aspect of the invention, a device for stimulating or modulating tissue comprises an elongate member having a longitudinal axis, a proximal end, and a distal end, and a first pair of adjacent annular stimulating regions. The first pair of annular stimulating regions comprises a proximal annular stimulating region disposed near the distal end of the elongate member, and a distal annular stimulating region disposed near the distal end of the elongate member. The distal annular stimulating region is closer to the distal end of the elongate member than the proximal annular stimulating region. The proximal annular stimulating region comprises a plurality of independently energizable electrodes adapted to deliver current into the tissue. Adjacent electrodes in the proximal annular stimulating region are separated from one another by an insulating member disposed on the elongate member, and the proximal annular stimulating region circumscribes the elongate member. The distal annular stimulating region comprises a plurality of independently energizable electrodes that are adapted to deliver current into the tissue. Adjacent electrodes in the distal annular stimulating region are separated from one another by an insulating member disposed on the elongate member, and the distal annular stimulating region circumscribes the elongate member. The distal annular stimulating region is axially separated along the longitudinal axis from the proximal annular stimulating member by a gap. A first internal electrical connector electrically couples a first electrode in the proximal annular stimulating region with a first electrode in the distal annular stimulating region. The first internal electrical connector is disposed within the elongate member, and the first internal electrical connector extends across the gap between the proximal and distal annular stimulating regions. A recording electrode is disposed in the gap between the proximal and distal annular stimulating regions. The recording electrode is adapted to record local tissue potentials from the tissue.

The elongate member may comprise a lumen extending between the proximal and distal ends thereof. The proximal annular stimulating region may completely circumscribe the elongate member.

The proximal annular stimulating region may consist of four electrodes, with adjacent electrodes separated from one another by an insulating member on the elongate member. The four electrodes may be disposed circumferentially around the elongate member. The proximal annular stimulating region may consist of three electrodes, with adjacent electrodes separated from one another by an insulating member on the elongate member. The three electrodes may be disposed circumferentially around the elongate member. The plurality of electrodes in the proximal annular stimulating region may each have a length in the direction of the longitudinal axis, and a width transverse thereto, and the length may be at least three times the width.

The distal annular stimulating region may completely circumscribes the elongate member. The distal annular stimulating region may consist of four electrodes, with adjacent electrodes separated from one another by an insulating member on the elongate member. The four electrodes may be disposed circumferentially around the elongate member. The distal annular stimulating region may consist of three electrodes, with adjacent electrodes separated from one another by an insulating member on the elongate member. The three electrodes may be disposed circumferentially around the elongate member. The plurality of electrodes in the distal annular stimulating region may each have a length in the direction of the longitudinal axis, and may have a width transverse thereto. The length may be at least three times the width.

The device may further comprise a second internal electrical connector electrically coupling a second electrode in the proximal annular stimulating region with a second electrode in the distal annular stimulating region. The second internal electrical connector may be disposed within the elongate member, and the second internal electrical connector may extend across the gap between the proximal and distal annular stimulating regions. The device may also have a third internal electrical connector electrically coupling a third electrode in the proximal annular stimulating region with a third electrode in the distal annular stimulating region. The third internal electrical connector may be disposed within the elongate member, and may extend across the gap between the proximal and distal annular stimulating regions. The first electrical connector may be integral with the first electrode in the proximal annular stimulating region or integral with the first electrode in the distal annular stimulating region.

The device may consist of a single recording electrode. The recording electrode may comprise an annular recording electrode completely circumscribing the elongate member. The device may further comprise a second recording electrode disposed in the gap between the proximal and distal annular stimulating regions. The second recording electrode may be adapted to record local tissue potentials from the tissue.

The device may further comprise a multiple contact connector electrically coupled with the plurality of annular stimulating regions and the recording electrode. The device may also comprise a second pair of adjacent annular stimulating regions, the second pair of annular stimulating regions adjacent the first pair and comprising a proximal annular stimulating region disposed near the distal end of the elongate member, and a distal annular stimulating region disposed near the distal end of the elongate member. The distal annular stimulating region may be closer to the distal end of the elongate member than the proximal annular stimulating region, and the proximal annular stimulating region in the second pair may comprise a plurality of electrodes adapted to deliver current into the tissue. Adjacent electrodes may be separated from one another by an insulating member disposed on the elongate member, and the proximal annular stimulating region in the second pair may circumscribe the elongate member. The distal annular stimulating region in the second pair may comprise a plurality of electrodes adapted to deliver current into the tissue, with adjacent electrodes separated from one another by an insulating member disposed on the elongate member. The distal annular stimulating region in the second pair may circumscribe the elongate member. The distal annular stimulating region in the second pair may be axially separated along the longitudinal axis from the proximal annular stimulating member in the second pair by a second gap. A second internal electrical connector may electrically couple a first electrode in the proximal annular stimulating region of the second pair with a first electrode in the distal annular stimulating region of the second pair. The second internal electrical connector may be disposed within the elongate member, and may extend across the second gap between the proximal and distal annular stimulating regions of the second pair. A second recording electrode may be disposed in the second gap between the proximal and distal annular stimulating regions of the second pair. The second recording electrode may be adapted to record local tissue potentials from the tissue.

A system for stimulating or modulating tissue may comprise the device for stimulating or modulating tissue as describe herein, and may also include an implantable pulse generator operatively coupled with the stimulating or modulating device. The system may further comprise an anchoring device that is adapted to removably couple the device to a patient's head.

In another aspect of the present invention, a device for stimulating or modulating tissue comprises an elongate member having a longitudinal axis, a proximal end, and a distal end. The device also comprises a first pair of adjacent annular stimulating regions. The first pair of annular stimulating regions comprises a proximal annular stimulating region disposed near the distal end of the elongate member, and a distal annular stimulating region disposed near the distal end of the elongate member. The distal annular stimulating region is closer to the distal end of the elongate member than the proximal annular stimulating region. The proximal annular stimulating region comprises a plurality of electrodes adapted to deliver current into the tissue, with adjacent electrodes separated from one another by an insulating member disposed on the elongate member. The electrodes of the proximal annular stimulating region have a length in the direction of the longitudinal axis and a width transverse thereto. The length is greater than the width but less than fifteen times the width, and the proximal annular stimulating region circumscribes the elongate member. The distal annular stimulating region comprises a plurality of electrodes adapted to deliver current into the tissue, with adjacent electrodes separated from one another by an insulating member disposed on the elongate member. Electrodes of the distal annular stimulating region have a length in the direction of the longitudinal axis and a width transverse thereto. The length is greater than the width but less than fifteen times the width, and the distal annular stimulating region circumscribes the elongate member. The distal annular stimulating region is axially separated along the longitudinal axis from the proximal annular stimulating member by a gap. A first internal electrical connector electrically couples a first electrode in the proximal annular stimulating region with a first electrode in the distal annular stimulating region. The first internal electrical connector is disposed within the elongate member, and extends across the gap between the proximal and distal annular stimulating regions. A recording electrode is disposed in the gap between the proximal and distal annular stimulating regions, and is adapted to record local tissue potentials from the tissue.

The device may further comprise a second pair of adjacent annular stimulating regions. The second pair of annular stimulating regions may be adjacent the first pair and may comprise a proximal annular stimulating region disposed near the distal end of the elongate member, and a distal annular stimulating region disposed near the distal end of the elongate member. The distal annular stimulating region may be closer to the distal end of the elongate member than the proximal annular stimulating region. The proximal annular stimulating region in the second pair may comprise a plurality of electrodes adapted to deliver current into the tissue, with adjacent electrodes separated from one another by an insulating member disposed on the elongate member. The electrodes of the proximal annular stimulating region in the second pair may have a length in the direction of the longitudinal axis and a width transverse thereto. The length may be greater than the width but less than five times the width, and the proximal annular stimulating region in the second pair may circumscribe the elongate member. The distal annular stimulating region in the second pair may comprise a plurality of electrodes adapted to deliver current into the tissue, with adjacent electrodes separated from one another by an insulating member disposed on the elongate member. The electrodes of the distal annular stimulating region may have a length in the direction of the longitudinal axis and a width transverse thereto, and the length may be greater than the width but less than five times the width. The distal annular stimulating region in the second pair may circumscribe the elongate member. The distal annular stimulating region in the second pair may be axially separated along the longitudinal axis from the proximal annular stimulating member in the second pair by a second gap. A second internal electrical connector may electrically couple a first electrode in the proximal annular stimulating region of the second pair with a first electrode in the distal annular stimulating region of the second pair. The second internal electrical connector may be disposed within the elongate member, and may extend across the second gap between the proximal and distal annular stimulating regions of the second pair. A second recording electrode may be disposed in the second gap between the proximal and distal annular stimulating regions of the second pair, and the second recording electrode may be adapted to record local tissue potentials from the tissue.

These and other embodiments are described in further detail in the following description related to the appended drawing figures.

BRIEF DESCRIPTION OF THE DRAWINGS

FIG. 1 illustrates one embodiment of a tissue monitoring and modulation probe.

FIG. 2 illustrates another embodiment of a tissue monitoring and modulating probe.

FIG. 3 illustrates yet another embodiment of a tissue monitoring and modulating probe.

FIG. 4 illustrates still another embodiment of a tissue monitoring and modulating probe.

FIGS. 21A-21D illustrate an additional exemplary embodiment, in which proximal and distal portions of a stimulating electrode are internally connected to allow favorable placement of an additional electrode suited for recording local tissue potentials.

FIGS. 28A-28D illustrate an embodiment of an individual stimulating electrode with structure suitable to serve as a component of a lead such as that illustrated in FIG. 27.

FIGS. 31A-31D illustrate still other embodiments of stimulation structures.

FIGS. 34A-34C illustrate another embodiment of stimulating and recording structures.

DETAILED DESCRIPTION OF THE INVENTION

Figure 5:
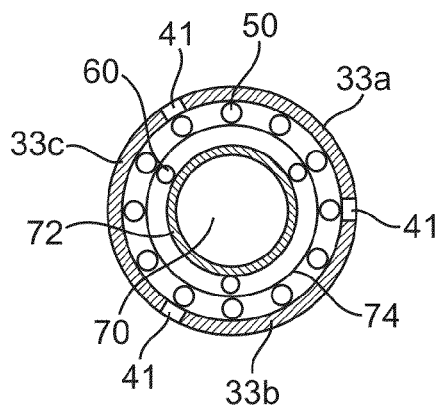
FIG. 5 illustrates a cross-section of a tissue monitoring and modulation probe.

In the drawings like numerals describe substantially similar components.

Probes and medical leads often have annular stimulating regions fixedly attached to their outer surface near their distal ends. The stimulating regions are arranged so as to pass electrical current from a remote source, into and through a tissue targeted for therapeutic stimulation, and back to the source. The return path for current is most commonly through the housing of the current source, but also commonly courses through the lead back to the source. When a transient electrical current passes through tissue with sufficient current density, it generates voltage gradients within the tissue. Clinically significant voltage gradients engage voltage sensitive dynamical elements in cell membranes related to signaling processes, such as voltage-gated ion-conducting channels, thereby generating or blocking action potential propagation within the tissue. Electrical current travels along a path of least resistance between electrodes of opposite polarity. In exemplary embodiments of the invention, such electrodes may all be parts of a single annular stimulating region, or may be distributed among two or more annular stimulating regions, and may include a distant surface, such as the housing of an instrumentation package or controller. Exemplary implanted locations of such a controller are the chest or the extracranial aspect of the skull. Active elements may communicate with the electrodes, so as to regulate and control the voltage applied to the electrodes, thereby controlling the current through a volume of tissue near the electrodes, in turn modulating cell signaling processes. Likewise, active elements may communicate with the electrodes, so as to regulate and control the current passing through the electrodes, with similarly controlled consequent effects on cell signaling.

A therapeutic advantage is obtained by controlling the electrical stimulation so as to maximize the desired modulatory effect, and to minimize undesired side effects. This corresponds to stimulating a target tissue with controlled timing and magnitude, and excluding stimulation of other tissue in the vicinity of the target tissue. The target tissue and other tissue in the vicinity of the target may occupy separate volumes of space, or may intermingle so as to occupy a shared volume of space. One mode of controlling therapeutic electrical stimulation is to generate voltage gradients sufficient to modulate cell signaling processes within the target tissue, but insufficient to modulate cell signaling processes within other tissue in the vicinity of the target. One way to achieve this goal is to generate a higher current density in the volume conductor comprised of the target tissue, compared to the current density of other tissue in the vicinity of the target. Another way to achieve this goal is to orient the current within the volume conductor, and thereby the voltage gradients within the volume conductor, so as to modulate neuronal processes within the target tissue in preference to modulating neuronal processes in the vicinity of the target tissue. Examples of controlling electrical stimulation so as to obtain a therapeutic advantage may include, but are not limited to, steering the electrical current, steering the electrical field surrounding the device, steering the field of stimulation, steering the field of neuromodulation, orienting electrical dipoles, orienting voltage gradients, and orienting a current density field.

One way to steer the field of electrical stimulation is to employ a lead with many stimulating electrodes, the more the better, distributed across the surface of a medical lead, and provide a means to selectively energize one or some subset of the electrodes in isolation from the others, in sequence with the others, or in coordination with the others. Such control of the field of electrical stimulation may be thought of as digital control, set control, or control by selection. An electrode, or an ensemble of electrodes is selected on the basis of their proximity to a therapeutic target. Therapeutic electrical stimulation is directed towards a target tissue by stimulating the electrode or electrodes closest to the target. An example of a cardiac pacemaker lead adapted to steer current by selectively energizing a subset from a collection of 6 electrodes, which together with interposed insulating surfaces circumscribe the lead, has been reported in the scientific and patent literature.

Another way to steer the field of the electrical stimulation is to divide an annular stimulating region into two pairs of electrodes, each member of a pair situated on the surface of a medical lead, positioned diametrically opposite to its companion. Such an arrangement can generate an electrical dipole oriented in any direction in a plane orthogonal to the elongate axis of a medical lead. An oriented electrical dipole can lead to an oriented field of current density in a volume conductor, which can in turn lead to an oriented voltage gradient, which can in turn lead to an oriented field of neuromodulation. The oriented field of stimulation may be generated by energizing each pair of electrodes by electrically independent circuits, with a current or voltage magnitude that is controlled in coordination. This simple method is sufficient for practice in the absence of constraints. Additional modes of current steering related to a medical lead with a plurality of stimulating regions, each region comprised of an ensemble of electrodes and interposed insulating regions which together circumscribe the lead, are described in patent and scientific literature.

In the presence of constraints, as described below, a preferable structure is to divide an annular stimulating region into three stimulation sites. This configuration may be coupled to current or voltage sources in such a way that a dipole may be generated along any direction in a plane. Three electrodes per annular stimulating region is the minimum number of stimulation sites per electrode required to orient a dipole along any direction in a plane. Using the minimum number of stimulation sites is also advantageous because it minimizes the number of conductors which must pass through the probe and permits maximum current density through any recording site to modulate the brain tissue. Consequently, this geometrical structure provides a superior ability to steer the field of electrical stimulation around a medical lead, compared to two pairs of electrodes aligned along orthogonal axes, as described in the preceding paragraph. Obtaining these advantages requires a different control scheme. Whereas two pairs of electrodes aligned along orthogonal axes may be controlled by two electrically independent circuits, with coordinated stimulus timing and magnitude, superior current steering through three electrodes in an annular stimulating region requires that the total current through one electrode be returned either selectively through one of the other electrodes, or divided in some proportion between the other two electrodes within the region. Such a structure of three electrodes can be considered to be three oriented pairs of electrodes with any two pairs sharing exactly one electrode between them. The dipole driving electrical current flow and electrical stimulation of a tissue may be oriented in any direction in a plane orthogonal to the long axis of the lead by controlling the timing, magnitude and polarity of the current passing through the three electrode pairs in coordination. Such control can be obtained expediently by electrically coupling the three pairs of electrodes to three electrical sources of electrical voltage or current.

Those skilled in the art will understand that an electrical dipole is comprised of two oppositely charged electrical monopoles. They will further appreciate that an electrical dipole generates an oriented electric field in the volume of space surrounding the dipole. They will further understand that if the volume of space surrounding the dipole is electrically conductive, that an oriented field of current will flow, and that the electrical field, voltage gradients within the electrical field, and current density in the volume conductor will all be consistent. They will further understand that creating distinct spatially oriented voltage gradients within an electrically excitable tissue, such as brain, nerve or muscle tissue, will create spatially distinct fields of stimulation. They will further understand that the orientation of the field of stimulation may further differentiate its effect by its alignment or misalignment with the spatial orientation of elongate cellular processes within the tissue, such as axons, dendrites and muscle fibers. They will further understand that the simplified model disclosed herein substantially describes the advantages of dividing a fixed electrode surface area into three stimulating sites circumscribing a medical lead, over dividing the surface area into four stimulating sites circumscribing the lead, for the purpose of creating an oriented field of stimulation near the lead. They will further understand that for the present purpose, complicating effects of electromagnetic radiation are small. Those skilled in the art will appreciate that the quantitative discussion which follows is not an exact model, but simplified explanation of how the present invention supports comparable performance to a comparison case known in the art, and superior with respect to the predictability of the ability to orient an electrical stimulation field at any angle. Embodiments of the present invention have the additional advantages of (1) better support for recording relevant electrical potentials, (2) a structure which is simpler to manufacture, and (3) compatibility with industry standard interfaces, thereby more simply serving as an interchangeable component of a brain stimulation and monitoring system.

Figure 14A:
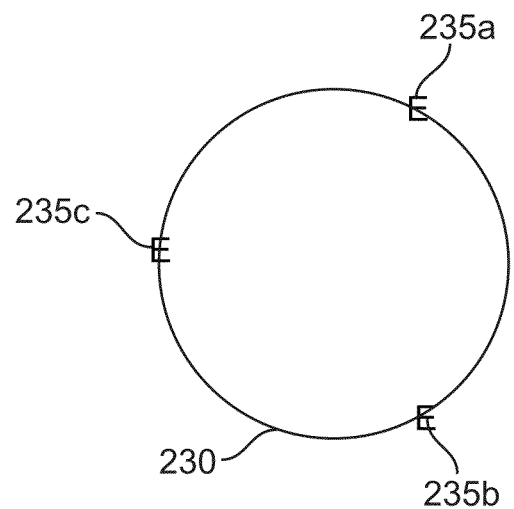
FIGS. 14A-14B illustrate a simplified geometrical model of exemplary embodiments supporting discussion of steering current by generating an oriented electrical field.
Figure 14B:
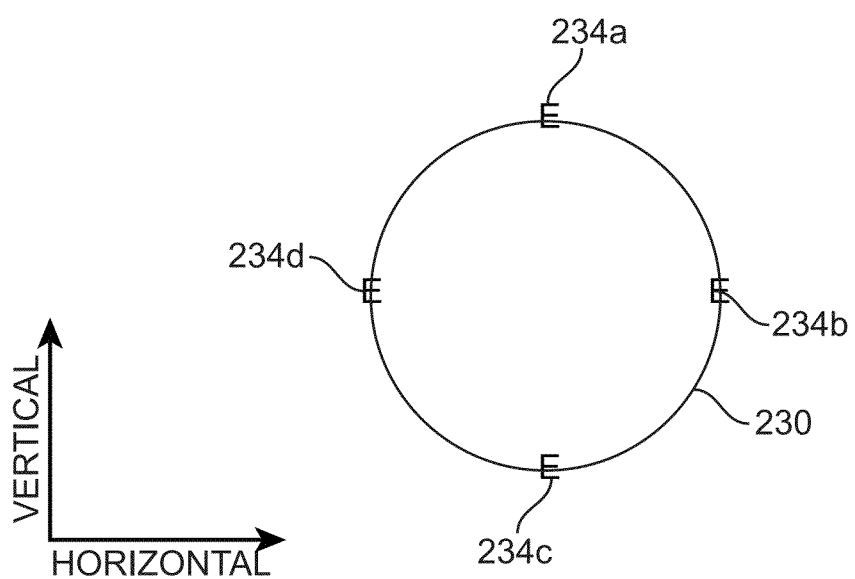

Consider the particular case that all of the electrodes in one broken ring, or circular ensemble, are energized identically and in coordination, in order to provide an unsteered stimulating effect similar to that produced by energizing a ring electrode, such as is common in the art. In this case, all of the stimulating surfaces in one ensemble of electrodes circumscribing the long axis of the lead are energized together, with the same magnitude of current or voltage, and with the same polarity relative to a neutral point where current is returned to the power source. It is common in the art for such a neutral part to communicate directly with the case of a programmable pulse generator (see for example reference 19 in FIG. 18). With reference to FIG. 14B, a source, or sources of equal magnitude and duration, are connected simultaneously to electrodes 234a, 234b, 234c and 234d. With reference to FIG. 14A, a source, or sources of equal magnitude and duration, is connected simultaneously to electrodes 235a, 235b, and 235c. If (1) the magnitude of the stimulation is constrained by the current density across the electrode surface, and (2) the surface area of the electrodes in a circular ensemble is substantially greater than the surface area of the insulating regions interposed between the stimulating elements, then one electrode, or an ensemble of any number of electrodes with the same net surface area will generate a substantially similar stimulation effect within the target tissue.

Consider the particular case that the electrodes within one circular ensemble or broken ring (also referred to herein as an annular stimulating region) are energized in coordination, with any anodes and cathodes, all members of the same ensemble, in such a way as to achieve the greatest magnitude of stimulation consistent with current density as a constraint. In practice, the amount of current which may pass through a brain stimulating electrode is limited by the ability of brain tissue to tolerate, without sustaining damage, injury pathology or harm due to passage of current across its interface with the tissue. Limiting the current which may pass through stimulating electrodes has the consequence of limiting the magnitude of the dipole driving an oriented current field, and the associated field of electrical stimulation within the tissue. A simplified model of how the current density constraint constrains the magnitude of the oriented dipole for the present invention and a more obvious comparison case is discussed below. The model supports a comparison of steering of the stimulation field by the present invention, with three concentric electrodes circumscribing a medical lead, with the more obvious case of four electrodes circumscribing a lead. The comparison calculations are based on the assumptions that angular extent of the each of the electrodes in the set of three is 120 degrees, while the angular extent of each electrode in the set of four is 90 degrees. It simplifies the calculation by considering current proportional to the area of each electrode to be sourced or sinked at the angular center of the electrodes. It analyzes only the plane orthogonal to the long axis of the lead. It considers other things to be equal between the two cases. Such other things include the axial extent of each electrode, the electrical resistance encountered by current flowing through a pair of electrodes, and the diameter of the elongate member of the lead.

Figure 15A:
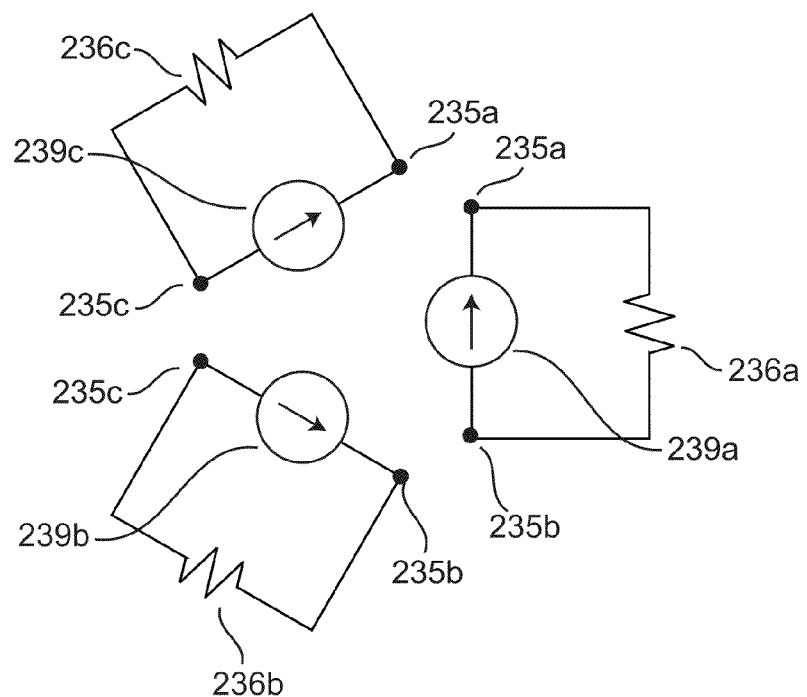
FIGS. 15A-15B illustrates a functional model of exemplary embodiments supporting discussion of generating an oriented electrical field.
Figure 15B:
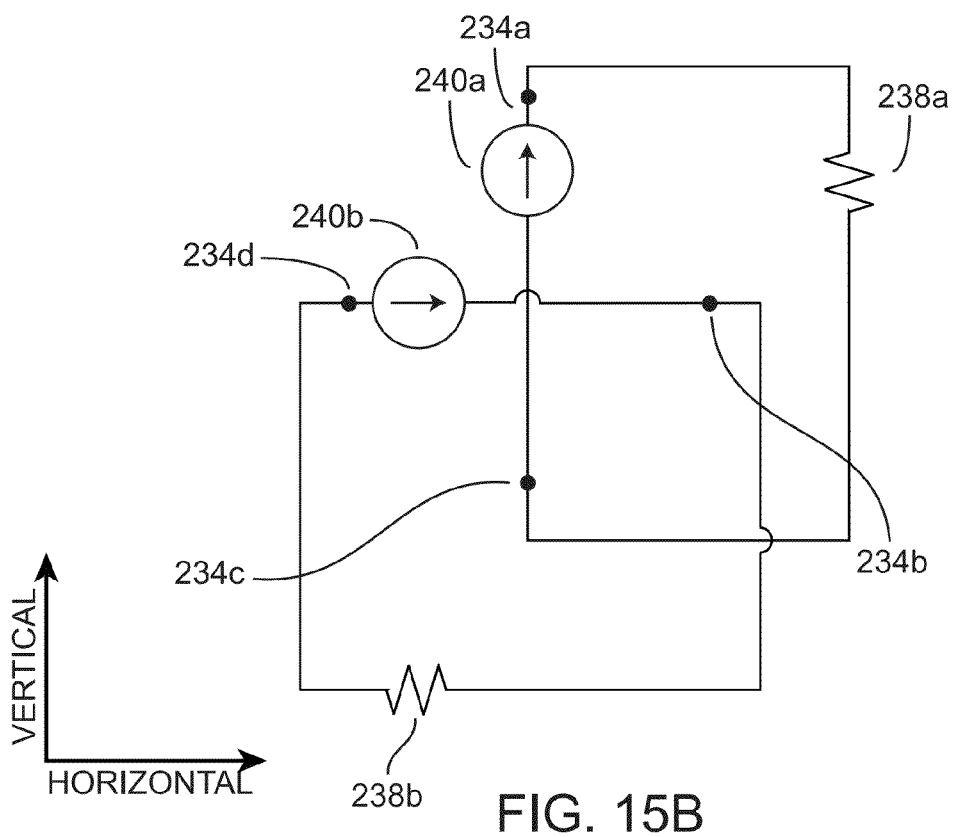
Figure 16:
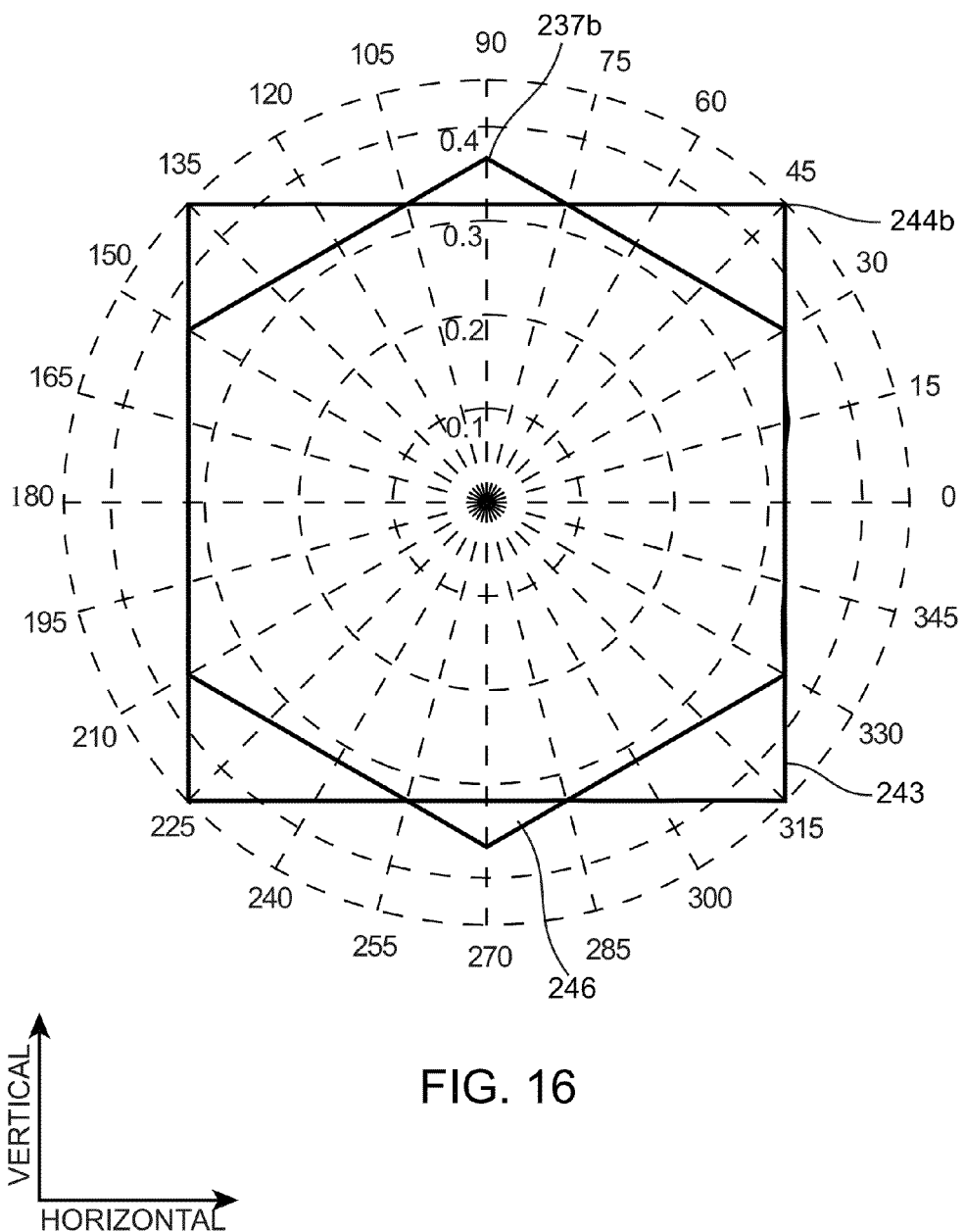
FIG. 16 compares the dipole orientation for exemplary embodiments and the comparison case illustrated in FIGS. 14A-14B and 15A-15B.

With reference to FIGS. 14B, 15B and 16, maximal stimulation is attained when one pair of adjacent electrodes is energized identically as an anode, with the remaining pair of adjacent electrodes energized identically as a cathode. For example, electrodes 234a and 234b could be energized as an anode, with electrodes 234c and 234d energized as a cathode. The orientation and magnitude of the dipole generated by such stimulation could be represented by a vector from the long axis of the lead 231 to the corner of the square 243, 244b. This mode affords the largest effect within the target tissue, because the effective single anode formed by two members of the ensemble of four, and the effective single cathode formed by the remaining members of the ensemble, have a large surface area. During stimulation, therefore, the anode and cathode have a correspondingly low current density. The electrode configuration discussed here can generate maximal stimulation in four directions, corresponding to positive and negative polarity along each of two orthogonal axes.

With reference to FIGS. 14A, 15A and 16, maximally oriented stimulation may be obtained with many specific patterns of stimulation. For example, electrode 235a could be energized as an anode, and electrode 235b could be energized as a cathode. The orientation and magnitude of the resulting dipole could be represented by a vector from the long axis of the lead 231 to a corner of the hexagon 246 in FIG. 15A, at point 237b. The magnitude of the maximal dipole for this invention is similar to the comparison case maximal dipole discussed in the preceding paragraph. The constraining current which may traverse one electrode 235 and into the tissue, with reference to FIGS. 14A and 15A, is less than the constraining current which may traverse a yoked pair of electrodes 234 into the tissue, with reference to FIGS. 14B and 15B. The electrode configuration modeled as in FIGS. 14A and 15B can generate maximal stimulation in six directions.

For a quantitative comparison, consider a simplified model of an exemplary embodiment of the present invention with three stimulation sites arranged as a broken ring circumscribing and encircling an elongate cylindrical lead. This is modeled by three point electrodes, separated by a circular arc of 120 degrees, as illustrated in FIG. 14A, with the three electrodes 235a, 235b, 235c depicted as the letter "E," in a plane orthogonal to the long axis of the lead. Consider the radius of the lead to be 0.635, in unspecified units and consider the magnitude of the current which could pass through each electrode to be ⅓ in units normalized so that a single electrode circumscribing the lead with the same axial extent would have a limiting current magnitude of 1. Consider three dipoles to be associated with electrical current passing through electrode pairs 235a and 235b (pair AB), electrodes 235a and 235c (pair AC) and electrodes 235b and 235c (pair BC). The sign and naming convention associates a positive sign with dipole AB when current flows out of electrode A and into electrode B as diagrammed in FIG. 15A. In this arrangement, the electrodes are spaced by 1.1 units with spacing in directions parallel to the horizontal and vertical axes as shown in the Table 1.

TABLE 1

| Electrode Pair | Horizontal Spacing | Vertical Spacing |
|---|---|---|
| AB | 0 | 1.10 |
| AC | 0.953 | 0.55 |
| BC | 0.953 | −0.55 |

The dipole generated by passing current through a pair of electrodes is estimated to be the product of the spacing between the electrodes and the normalized current. For example the maximum dipole magnitude that could be generated by electrode pair AB is the vector sum of zero along the horizontal axis, and the product of 1.1 (spatial separation) and ⅓ (current limit) for a dipole magnitude of 0.367 along the vertical axis. Positive current flow would orient the dipole in the upwards direction, and negative current flow would orient the dipole in the downwards direction. If three current sources are configured to separately regulate the current through the three electrode pairs, the resultant dipole is the sum of the dipoles generated by the three current sources subject to the constraint that the net current through any electrode is less than or equal to the maximum permitted. Because the three component dipoles are oriented along non-orthogonal axes, the three current sources may be coordinated with many different settings in order to produce a resultant dipole of a specified orientation and magnitude. With these conventions, the component dipoles, magnitude of the net current through each electrode, resultant dipole is presented in Table 2 for several example orientations. The dipole magnitude for this case and a comparison case are depicted in FIG. 16.

TABLE 2

| Angle (degrees) | AB current | AC current | BC current | Electrode A current magnitude, normalized | Electrode B current magnitude, normalized | Electrode c current magnitude, normalized | Resultant depole magnitude |
|---|---|---|---|---|---|---|---|
| 0 | 0 | 0.167 | 0.167 | .5 | .5 | 1 | .318 |
| 30 | 0.0 | 0.333 | 0.0 | 1 | 0 | 1 | .367 |
| 45 | 0.141 | 0.192 | 0.052 | 1 | .268 | .732 | 329 |
| 60 | 0.164 | 0.169 | −0.003 | 1 | .5 | .5 | .318 |
| 90 | 0.333 | 0.0 | −0.0 | 1 | 1 | 0 | .367 |

TABLE 2-continued

| Angle (degrees) | AB current | AC current | BC current | Electrode A current magnitude, normalized | Electrode B current magnitude, normalized | Electrode c current magnitude, normalized | Resultant depole magnitude |
|---|---|---|---|---|---|---|---|

Next, consider a comparison case with four stimulation sites arranged as a broken ring circumscribing and encircling an elongate cylindrical lead. This is modeled by four point electrodes, separated by a circular arc of 90 degrees, as illustrated in FIG. 14B, with the four electrodes 234a, 234b, 234c, 234d depicted as the letter "E," in a plane orthogonal to the long axis of the lead. As before, consider the radius of the lead to be 0.635, in unspecified units and consider the magnitude of the current which could pass through each electrode to be ¼ in units normalized so that a single electrode circumscribing the lead with the same axial extent would have a limiting current magnitude of 1. Because of the smaller angular extent, the limiting current through an electrode is less for this comparison case than for the case corresponding to the exemplary embodiment of present invention. Consider two dipoles to be associated with electrical current passing through electrode pairs 234a and 234c (pair AC), and electrode pair 234b and 234d (pair BD). The sign and naming convention are as in the preceding paragraph. In this arrangement, the electrodes are spaced by 1.27 units with spacing in directions parallel to the horizontal and vertical axes as shown in Table 3.

TABLE 3

| Electrode Pair | Horizontal Spacing | Vertical Spacing |
|---|---|---|
| AC | 0 | 1.27 |
| BD | 1.27 | 0 |

The dipole generated by passing current through a pair of electrodes is estimated to be the product of the spacing between the electrodes and the normalized current. For example the maximum dipole magnitude that could be generated by electrode pair AB is the vector sum of zero along the horizontal axis, and the product of 1.27 spatial units and ¼ current units for a dipole magnitude of 0.318 along the vertical axis. Positive current flow would orient the dipole in the upwards direction, and negative current flow would orient the dipole in the downwards direction. If two current sources are configured to separately regulate the current through the three electrode pairs, the resultant dipole is the sum of the dipoles generated by the three current sources subject to the constraint that the net current through any electrode is less than or equal to the maximum permitted. Because the two component dipoles are oriented along orthogonal axes, the two current sources may be coordinated in one unique combination in order to produce a resultant dipole of a specified orientation and magnitude. The dipole magnitude for this comparison case and the case corresponding to the exemplary embodiment of the present invention are depicted in FIG. 16.

TABLE 4

| Angle (degrees) | AC current | BD current | Electrode A and C current, normalized | Electrode B and D current, normalized | Resultant dipole magnitude |
|---|---|---|---|---|---|
| 0 | 0 | 0.250 | 0 | 1 | .318 |
| 30 | 0.145 | 0.250 | .579 | 1 | .367 |

TABLE 4-continued

| Angle (degrees) | AC current | BD current | Electrode A and C current, normalized | Electrode B and D current, normalized | Resultant dipole magnitude |
|---|---|---|---|---|---|
| 45 | 0.250 | 0.250 | 1 | 1 | .449 |
| 60 | 0.250 | 0.145 | 1 | .578 | .367 |
| 90 | 0.250 | 0 | 1 | 0 | .318 |

Note that the midpoints of the dipoles generated along the three axes are not coincident with the long axis of the lead 231, but are offset to the midpoint of a line segment between the electrode locations. Such a shift further differentiates the current field generated by stimulating a pair of electrodes, corresponding to a further shift in the field of electrical stimulation within the target tissue. This corresponds to a greater steering effect by the present invention compared the reference case discussed in the preceding paragraph. Such an off axis steering effect could be obtained using the reference configuration diagramed in FIG. 14, by energizing two adjacent electrodes 234 with opposite polarity. This would shift the field of stimulation off the long axis of the lead, but maximum stimulus magnitude would be lower than in the exemplary embodiment of the present invention, because the center of action of two adjacent electrodes 234 is closer together than for two electrodes 235, and the surface area of two electrodes 234 is less than the surface area 235.

The results illustrated in FIG. 16 expand upon the example calculations presented in Tables 2 and 4, illustrating the computations for dipole orientations from 0 to 355 degrees in 5 degree increments. FIG. 16 compares dipole magnitude 246 for the case of three electrodes arranged in a ring, together with interposed insulating regions circumscribing the lead, to the comparison magnitude 243 for the case of four electrodes arranged in a ring, together with interposed insulating regions circumscribing the lead. The magnitude of the dipole is similar in the compared cases. For a fixed placement of the lead, there will be some directions in which one or the other case can generate a greater oriented dipole. For the illustrated example, the case of three electrodes circumscribing the lead generates a greater dipole magnitude for orientations near direction 90 degrees (237b), and also in the opposite orientation near 270 degrees. The case of four electrodes circumscribing the lead generates a greater dipole magnitude near an orientation of 45 degrees 244b, and also near 135 degrees, 225 degrees and 243 degrees. The maximum possible dipole generated case of four electrodes circumscribing the lead is greater than for the case of three electrodes circumscribing the lead. Over an angular range of about 120 degrees, comprised of a range near 0 degrees and a range near 180 degrees, the magnitude of the dipole generated by the two cases is the same.

Referring now to FIG. 1, a tissue modulating and monitoring probe is illustrated. It is a cylindrical probe, with a flexible probe body 10 and an optional multiple contact connecting terminal 20a. Additional details on multiple contact connecting terminals are disclosed in U.S. Pat. No. 7,583,999, the entire contents of which are incorporated herein by reference.

Other connectors may be used and are well known in the art. At the distal end of the probe 30a there are one or more broken annular rings of stimulating sites. The stimulating sites may be aligned with matching angular position on all rings, or may be offset to different angular positions on different rings. There are also one or more circumferential electrode bands suitable for recording local field potentials, and a recording electrode at or near the most distal point. In this preferred embodiment, the maximum diameter of the multiple contact terminal 20a is the same as the diameter of the flexible probe body 10.

In this embodiment, at four axial positions, three stimulation sites 33a, 33b, 33c, 34a, 34b, 34c, 35a, 35b, 35c, 36a, 36b, 36c are arranged as broken rings, for a total of 12 stimulation sites. These are better seen in the cross-sectional views of FIGS. 5-12. Also in this embodiment are three recording bands 37, 38, 39 arranged in the gaps between the broken rings. The size of the recording sites is suitable for recording local field potentials, with an exposed area ranging from about 0.0005 mm$^2$ to about 0.5 mm$^2$ but the area could be up to about 0.8 mm$^2$. Some embodiments have smaller recording sites that improve extracellular recordings of action potentials. Such recording sites range in exposed area from about $1.9 \times 10^{-5}$ mm$^2$ to about 0.002 mm$^2$, but they could be as large as about 0.1 mm$^2$. The form of the recording sites could be the bare end of an insulated wire, a thin film, a metal pad, or an insulated region with a portion of the insulation removed to expose an electrical conductor within the wall of the device. Alternative embodiments may have no recording rings, or may have more recording rings. Additional recording rings or point electrodes may be located along the probe body 10 or at the probe tip 32. The embodiment does not restrict the alignment of the recording electrodes (bands and/or points) with respect to the stimulation sites. Providing diverse treatment options each offering different tradeoffs between therapeutic effects and side effects serves the interest of patients seeking to achieve the best balance of outcomes. The embodiments in this disclosure describe structures by which not only more options can be provided, but superior options can be provided.

The preferred embodiment includes a nonconductive gap of at least 100.mu.m between stimulating and recording surfaces, and between recording surfaces, to reduce shunting and improve the isolation of recorded signals. Other embodiments may reduce this gap at some positions about the electrode surfaces. It is desirable that electrical signals traversing through the probe do not interfere with each other. It is especially desirable that the high level electrical stimulation signals not interfere with the low level recording signals. Therefore, it is preferable that the conductors carrying recording signals lay in an inner helix, while conductors carrying stimulation signals lay in an outer helix. The pitch of the two helices may be the same or may be different, so that no pair of stimulation and recording conductors traverse adjacent paths for an appreciable distance. This minimizes capacitive coupling between any stimulating conductors and any recording conductors. In other embodiments, a conductive coating may be applied to the outside of the helix of recording conductors. This can be grounded to decrease electromagnetic interference between the two types of conductors. In yet another embodiment, a metal foil, which may be grounded, is wrapped between the inner and outer wire helices.

In other embodiments, the conductors carrying recorded signals lay between conductors carrying electrical stimulation signals. This embodiment has the advantage that the conductors lay in a single lamina and can be more compact and more flexible, although in some instances this embodiment may have the disadvantage that when stimulating current modulates a stimulating conductor, the stimulation signal may couple into adjacent recording conductors. Note that not all of the stimulus conductors are required to carry a current at any instant. In many uses of the probe, some of the recording conductors will therefore be well separated from active stimulating conductors at any instant. In another embodiment, the stimulating wires and recording wires course as adjacent groups of conductors in a helix.

The wires should be mechanically strong and electrically conductive. Suitable materials include alloy MP35N (cobalt chrome alloy), stainless steel, and tungsten or tungsten alloy wire which has been gold plated to facilitate continuity with the stimulation sites and to the extra-cranial connector. It is important that the material be minimally magnetic to maximize MRI compatibility.

Stimulation sites are made of a relatively inert material which maximizes safe charge transfer, such as platinum, iridium or an alloy of platinum and iridium. The body of the probe is coated by a biocompatible polymer, such as silicone rubber or polyurethane, which supports bending with a short radius of curvature where the probe exits the cranium.

FIG. 2 illustrates an alternative embodiment of the probe 30b. Probe 30b is similar to the probe 30a of FIG. 1 except that it adds ports 40 which may permit chemical substances to enter or leave the probe lumen. The ports 40 may be covered by a semi-permeable membrane. Alternatively a chemically controlled gating mechanism, such as a chemically reactive hydrogel, may be placed near the ports. Such a hydrogel can swell or contract depending upon the chemical composition of the adjacent medium. The gating mechanism may operate based on bulk swelling and occlusion of the port, or the hydrogel may be formed with a mechanical accessory structure. An example of such as structure includes a bimorph beam as described by R. Bashir, J. Z. Hilt, O. Elibol, A. Gupta, and N. A. Peppas in "Micromechanical Cantilever as an Ultrasensitve pH Microsensor," published in Applied Physics Letters, 81(16):3091-3093, 2002. Another example includes a surface covering fenestrated with microports as disclosed by A. Baldi, M. Lei, Y. Gu, R. A. Siegel and B. Ziaie in an article entitled "A Microstructured Silicon Membrane with Entrapped Hydrogels for Environmentally Sensitive Fluid Gating," published in Sensor and Actuators B, 114(1):9-18, 2006, or another example includes a pad which displaces elements suited to forming an occlusive seal as described by A. Baldi, Y. Gu, P. E. Loftness, R. A. Siegel and B. Ziaie in "A Hydrogel-Actuated Environmentally Sensitive Microvalve for Active Flow Control," published in the Journal of Microelectromechanical Systems, 12(5):613-621, 2003. The entire contents of these references are incorporated herein by reference.

Since the hydrogels may be formulated such that their volume has different chemical dependencies, different hydrogels may be associated with ports at different pre-determined positions on the lead, so that drugs may be delivered selectively to pre-determined positions on the probe. Likewise, samples of the extra-cellular space or cerebral spinal fluid (CSF) may be obtained from pre-determined positions on the probe. Examples of chemical gating mechanisms that are controlled directly by pH include those described previously in "Micromechanical Cantilever as an Ultrasensitve pH Microsensor. Gating mechanisms controlled by the presence of carbon dioxide via a relationship to pH include those described by R. Steege, H. Sebastiaan, W. Olthuis, P. Bergveld, A. Berg, and J. Kolkman in "Assessment of a New Prototype Hydrogel CO2 Sensor; Comparison with Air Tonometry," as published in The Journal of Clinical Monitoring and Computing 21(2):83-90, 2007. Other examples of gating mechanisms controlled by the presence of glucose are disclosed by Theeuwes et al. in U.S. Pat. No. 6,997,922. The entire contents of the above listed references are incorporated herein by reference.

FIG. 3 illustrates an alternative embodiment of probe 30c in which the probe tip 32a is electrically conductive, serving as an additional stimulation site. This could serve as a conventional stimulation site, supporting monopolar and bipolar stimulation. In conjunction with a distal ring of stimulation sites 36a-36c it forms a group of stimulation sites centered on the vertices of a tetrahedron, supporting steering of the current near the tip in three dimensions. The embodiment of FIG. 3 also has an additional recording electrode 42 between stimulating electrodes 36a-36c and distal stimulating electrode 32a. Also, multiple contact connecting terminal 30c has a plurality of electrical contacts axially spaced along two hemi-cylidrical or D-shaped connectors, as further disclosed in U.S. Pat. No. 7,583,999 previously incorporated by reference.

FIG. 4 illustrates an alternative embodiment of the probe, 30d, demonstrating that the multiple contact terminal 20d need not have the same diameter as the probe body 10. Here, contact terminal 20d is a larger diameter cylindrical shaped plug with receptacles for coupling the probe 30d with the rest of the monitoring and modulation system. This embodiment illustrates that the exposed surfaces of recording electrodes need not be circular, but may be configured as recording points 43. Alternative embodiments may include multiple recording sites, some configured as rings, and others configured as points. In other embodiments the recording electrodes may take other shapes, including squares, rectangles or irregular shapes. In yet another alternative embodiment, the multiple contact terminal may allow for a lumen or conduit for the passage fluid within the probe. Fluid may pass in one or more lumens, and may flow into or out of the brain, or both.

FIG. 5 illustrates an axial cross-sectional view of an embodiment, at section line 101 in FIG. 1. In the this embodiment the central lumen 70 is surrounded by a tube 72 made of a biocompatible polymer, such as PEEK (poly ether ether ketone), polyurethane, silicone rubber or polyimide. In alternative embodiments the lumen is a polymer coating, and the insulated recording conductors 60 may reside in the inner lumen. Recording conductors 60 are wound in a helix from the recording sites to their termination at the contact terminal 20. Likewise, the stimulating conductors 50 are wound in a helix from the stimulation sites to their termination at the contact terminal 20. In a preferred embodiment, the stimulating conductors 50 have larger size than the recording conductors 60 because resistive losses are a greater concern for the stimulating conductors 50, but all conductors may be of the same or similar dimension in alternative embodiments. In a preferred embodiment, the pitches of the recording conductor helix and the stimulating conductor helix are distinct from each other, to decrease the average capacitive coupling between the wires. In alternative embodiments the helices could have the same pitch. The two helices may have the same or opposite orientation (one clockwise, the other counter-clockwise). Conductors 50, 60 are embedded in a flexible polymer, and are insulated in the preferred embodiment, but may or may not rely on the surrounding polymer for insulation in an alternative embodiment. In the preferred embodiment, a layer of electrically conductive material 74 is interposed between the recording and stimulating conductors, which may be attached to a low impedance electrical reference. Alternative embodiments may use layer 74 or the central lining of the central lumen 72 as an internal stimulating electrode. Alternative embodiments may omit this layer 74 to simplify manufacturing. Stimulation sites 33a-33c lay on the surface of the probe, with gaps of nonconductive material 41 between them. The stimulation sites 33a-33c may be in the form of sections of a tube adhered to the probe, and welded or riveted to the conductors 50, or may be fabricated with thin film technology. Examples of thin film technology that could be used to fabricate the probe are described, for example, in U.S. Pat. Nos. 7,051,419 and 7,047,082 the entire contents of which are incorporated herein by reference. The conductors 50, 60 in FIG. 5 are shown as having a circular profile to suggest transversely cut round wires, but alternative forms could use shaped wires such as those having a square, rectangular or elliptical cross-section, or thin film technologies may be used for the conductors. FIG. 5 shows 12 stimulating conductors 50 and recording conductors 60, but alternative embodiments could have more or fewer conductors, corresponding to the number of stimulating and recording sites.

Figure 6:
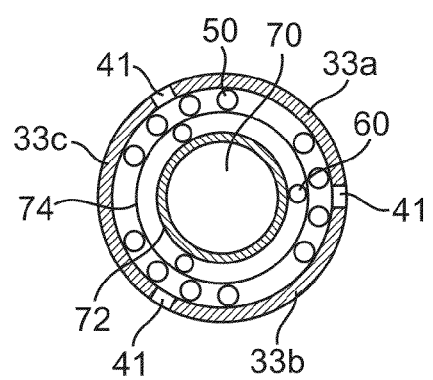
FIG. 6 shows a cross-section of an alternative embodiment of a monitoring and modulation probe.

FIG. 6 illustrates an alternative embodiment, in which the stimulating conductors 50 are arranged in groups rather than uniformly spaced around the circumference of the probe. Three groups of four are illustrated, but alternatively the conductors could be arranged in 4 groups of three. Such embodiments could allow for ports communicating between the central lumen 70 and the outside of the probe, or for improved flexibility of the probe in conjunction with reduced wall thickness between groups of conductors.

Figure 7:
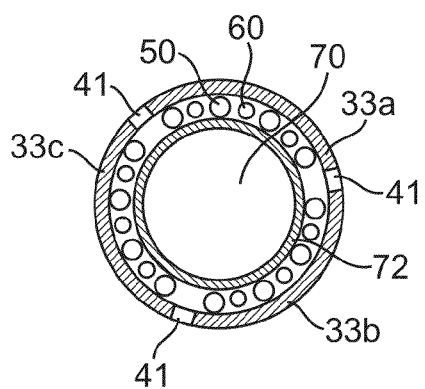
FIG. 7 shows a cross-section of yet another embodiment of a monitoring and modulation probe.

FIG. 7 illustrates an axial cross-sectional view of an alternative embodiment, at section line 101 in FIG. 1. In this embodiment, the stimulating and recording conductors are in the same annular space of the probe, unlike prior embodiments where the conductors are separated. Because this embodiment places both conductors in the same annular space, the central lumen 70 may be larger. In a preferred embodiment the stimulating conductors 50 and recording conductors 60 alternate around the helix, but in alternative embodiments the stimulating conductors and recording conductors could course as separate groups. In alternative embodiments, there may be additional conductors between the stimulating 50 and recording 60 conductors, which may be connected to the point of electrical neutrality. In alternative embodiments, the tube 72 may be coated with an electrically conductive material, which may be connected to the point of electrical neutrality.

Figure 8:
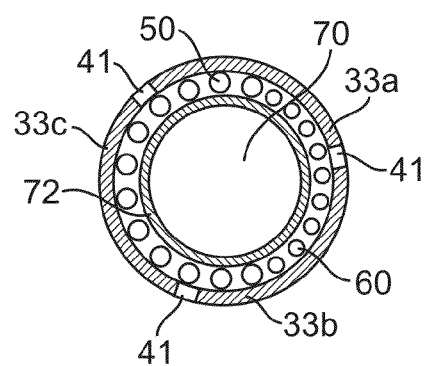
FIG. 8 shows a cross-section of still another embodiment of a monitoring and modulation probe.

FIG. 8 illustrates an alternative embodiment wherein the recording conductors 60 and stimulating conductors 50 are separated into groups. This embodiment has the advantage of reduced opportunities for undesirable capacitive coupling between stimulating and recording conductors compared to the embodiment illustrated in FIG. 7, but increases the opportunities for undesirable capacitive coupling between separate recording conductors.

Figure 9:
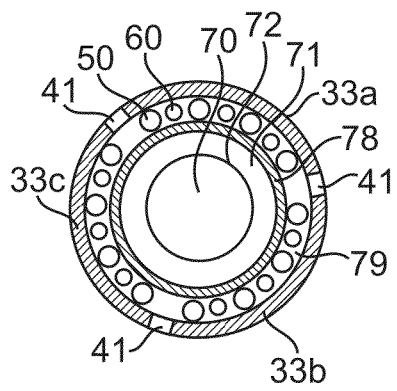
FIG. 9 shows another cross-section of another embodiment of a monitoring and modulation probe.

FIG. 9 illustrates an embodiment with dual lumens, central 70 and annular 71, to permit delivery or sampling of a fluid (gas or liquid) substance or drug, or sampling of a liquid or volatile substance. The lumens may communicate with ports, shown as 40 in FIGS. 2 and 13A-13C, and such communication may be electrically or chemically gated. The distal ends of the lumens may be closed, permeable, selectively permeable, or open, to release the lumen contents or some fraction or portion of the lumen contents. The distal ends of the two lumens may communicate with each other, so that one delivers a liquid containing a drug such a levodopa, or a gaseous medium with bioactive effects such as carbon monoxide or nitrous oxide, and another lumen retrieves the medium, after an opportunity to exchange a substance or substances with the medium near ports 40 or other openings in the probe. Other therapeutic agents that may be delivered are well known in the art, such as those disclosed in U.S. Pat. Nos. 6,094,598 and 6,227,203 both of which, the entire contents are incorporated herein by reference and often, extracellular fluid such as cerebral spinal fluid (CSF) is sampled. In this embodiment, conductors for electrical stimulating and recording course together within an additional annulus 79 created by an additional wall 78 in the probe.

Figure 10:
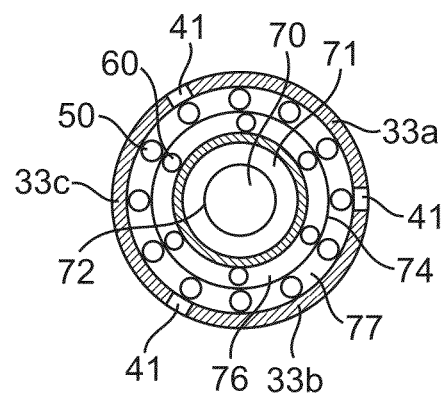
FIG. 10 shows yet another cross-section of an embodiment of a monitoring and modulation probe.

FIG. 10 illustrates an arrangement similar to that in FIG. 9, except that the conductors for stimulating and recording course through two separate annular rings 76 and 77, both concentric to the inner two lumens 70 and 71. In other embodiments, there may be more than two lumens, and the lumens need not be concentric.

Figure 11:
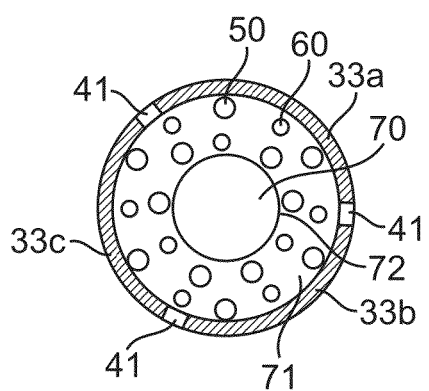
FIG. 11 shows still another cross-section of another embodiment of a monitoring and modulation probe.

FIG. 11 illustrates an arrangement similar to that in FIG. 9, except that there is a single lumen 72. Additionally, conductors 50 and 60 are randomly oriented and therefore may allow the probe to be more easily fabricated as opposed to a probe with conductors in a defined pattern.

Figure 12:
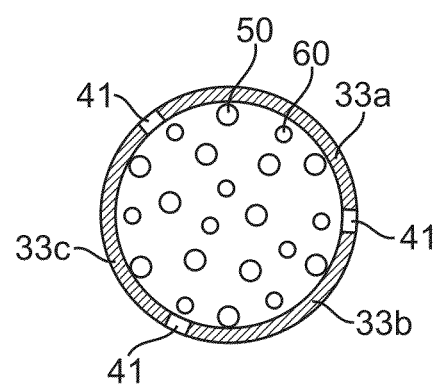
FIG. 12 shows another cross-section of another embodiment of a monitoring and modulation probe.

FIG. 12 illustrates an arrangement with no lumen for either a guide wire, or for supporting mass transfer. The conductors course together through the center of the probe.

Figure 13A:
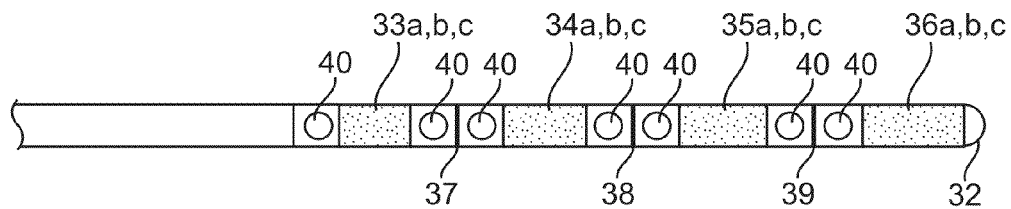
FIGS. 13A-13C highlight the recording and stimulating regions of an exemplary embodiment of a monitoring and modulation probe.
Figure 13B:
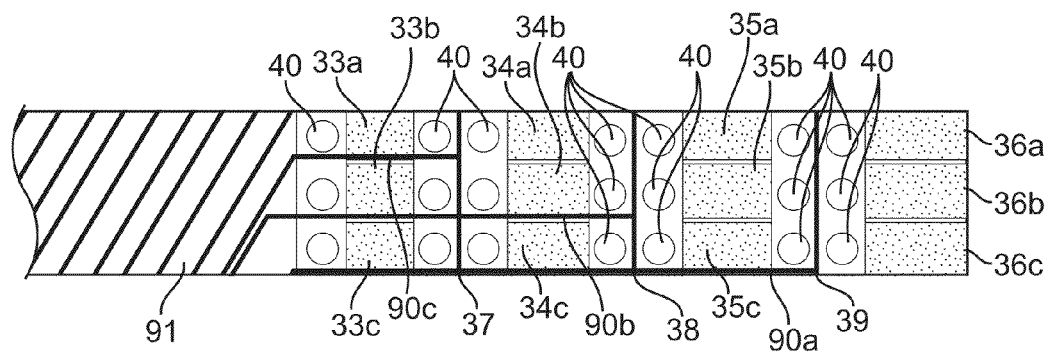
Figure 13C:
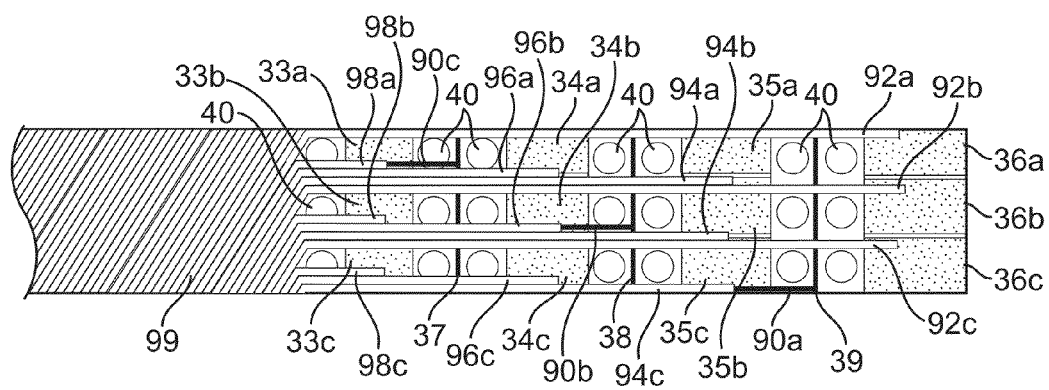

FIGS. 13A-13C illustrate an arrangement for the stimulating and recording conductors, similar to the embodiments illustrated in FIG. 2. FIG. 13A shows a probe having four regions of stimulating electrodes 36a-36c, 35a-35c, 34a-34c and 33a-33c, with each region having three independent stimulation sites. Additionally, the probe in FIG. 13A has recording electrodes 37, 38 and 39 as well as ports 40. The probe of FIG. 13A is shown in FIGS. 13B-13C with the circumference of the probe unwrapped, such that the upper edge and the lower edge of the conductors are actually continuous with each other. In the region of the probe tip, the conductors course in the axial direction, and turn to form helical windings along the probe body. FIG. 13B shows the recording electrode conductors 90a, 90b and 90c coursing in the axial direction near the probe tip and then turning to form helical windings along the probe body. FIG. 13C illustrates a similar pattern for stimulating electrode conductors 92a, 92b, 92c, 94a, 94b, 94c, 96a, 96b, 96c and 98a, 98b, 98c.

Figure 17:
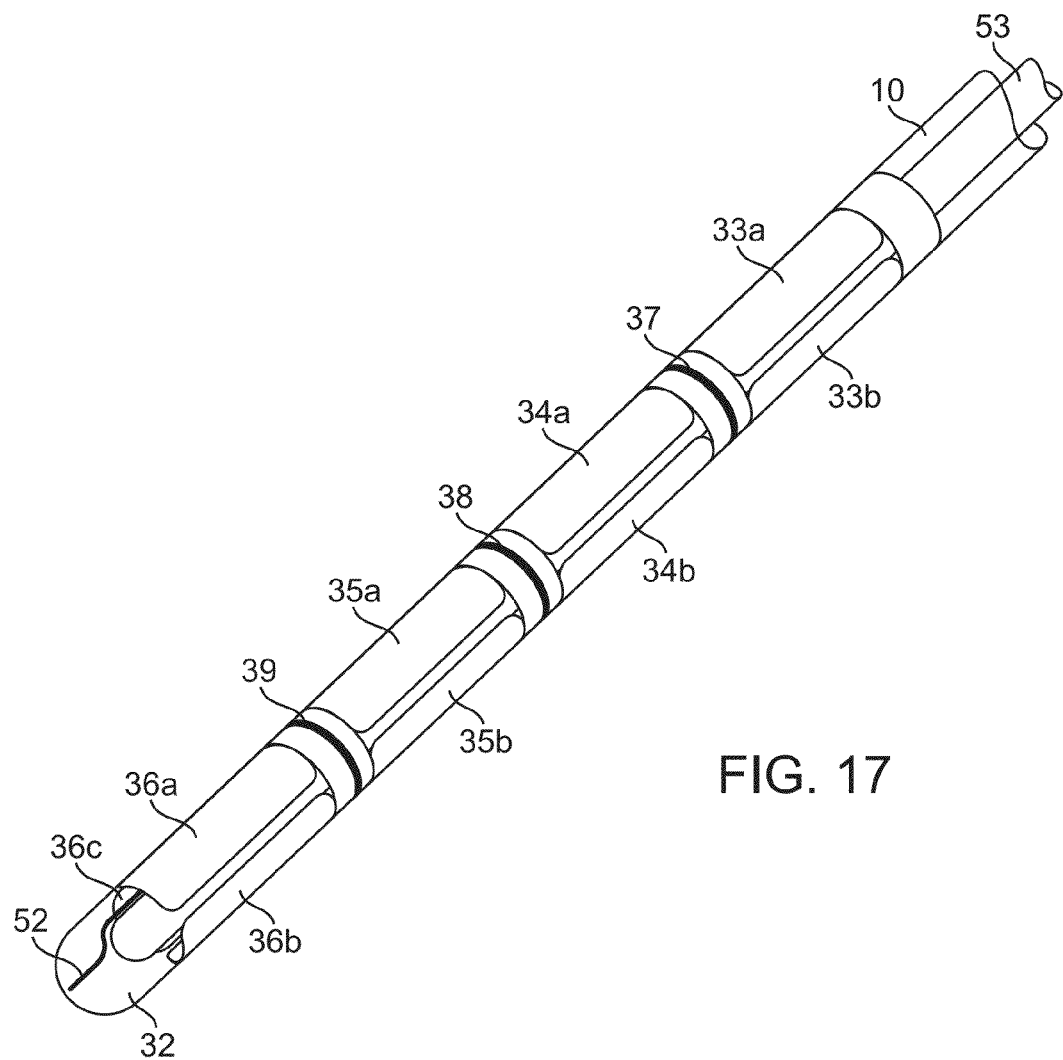
FIG. 17 shows a perspective view of an embodiment of a brain monitoring and modulation probe.

FIG. 17 shows a perspective view of a monitoring and modulation lead. In FIG. 16, four stimulation regions on the lead each contain three independent stimulation electrodes. All three stimulation electrodes 36a, 36b, 36c are only visible on the distal-most region. Two stimulating electrodes are visible in the other regions of the lead including 35a, 35b, 34a, 34b, 33a, 33b. Additionally, the lead has three recording electrodes 37, 38 and 39 as well as an additional recording electrode 52 near the distal lead tip 32. An inner shaft 53 is contained within lead body 10 and may be adapted to accommodate guidewires, stylets, lumens, etc. previously described herein.

Figure 18:
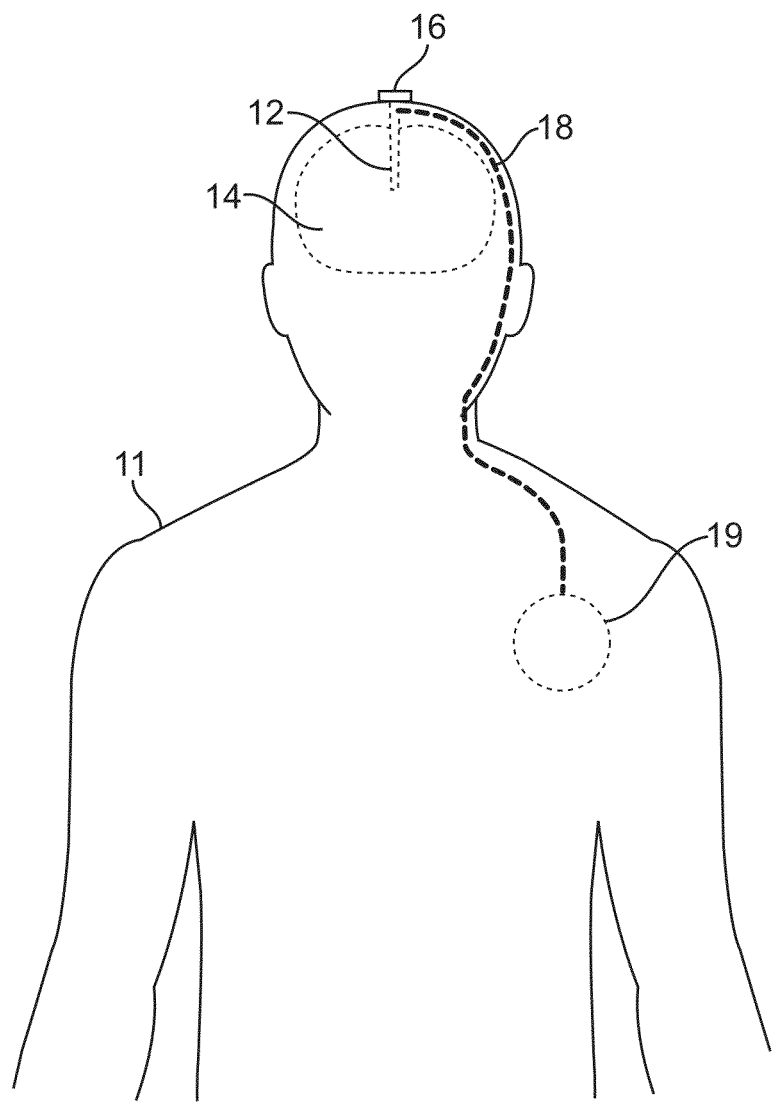
FIG. 18 shows a brain monitoring and modulation probe implanted into a patient's head.

FIG. 18 shows a monitoring and modulating probe or lead 12 secured to the skull of a patient 11 with a fixture 16 and implanted into brain tissue 14. An extension lead 18 couples the probe 12 with a controllable pulse generator 19. The lead often runs under the patient's skin, although it may not and the controllable pulse generator 19 may be implanted or it may remain external to the body of the patient 11. Additional details on a fixture for securing the probe to the skull are disclosed in U.S. Patent Publication No. 2009/0088826, the entire contents of which are incorporated herein by reference.

Table 5 below summarizes data collected that demonstrate that different functional stimulation effects can be achieved by stimulating different stimulation sites around an annular ring. A lead similar to that illustrated in FIG. 17 was inserted into the basal ganglia of an anesthetized cat. The stimulating sites in the most distal annular ring (36a, 36b and 36c) were energized together and independently to electrically stimulate the brain. The ground was placed in the temporalis muscle. Electrical stimulation of sufficient magnitude evoked a response in either the ipsilateral or contralateral or both facial muscles. Stimulation magnitude was delivered in voltage steps, and the motor response was graded on a rank-ordered scale (NR—No Response; THR, Response Threshold; larger numbers correspond to larger magnitude of suprathreshold responses). When site 36a was stimulated alone, the response threshold for ipsilateral movement was lower than for contralateral movement. When site 36b was stimulated alone, the response threshold for ipsilateral and contralateral movement was the same. When site 36c was stimulated alone, the threshold for contralateral movement was lower than for ipsilateral movement. When all three sites were stimulated simultaneously, the threshold for ipsilateral movement was lower than for contralateral movement, but the threshold for both ipsilateral and contralateral movement was lower than with stimulation of any single site. Data from this testing is summarized in Table 5 below, and this pattern of differential stimulation thresholds demonstrates that stimulating different sites within an annular ring steers electrical current within the brain.

Figure 19A:
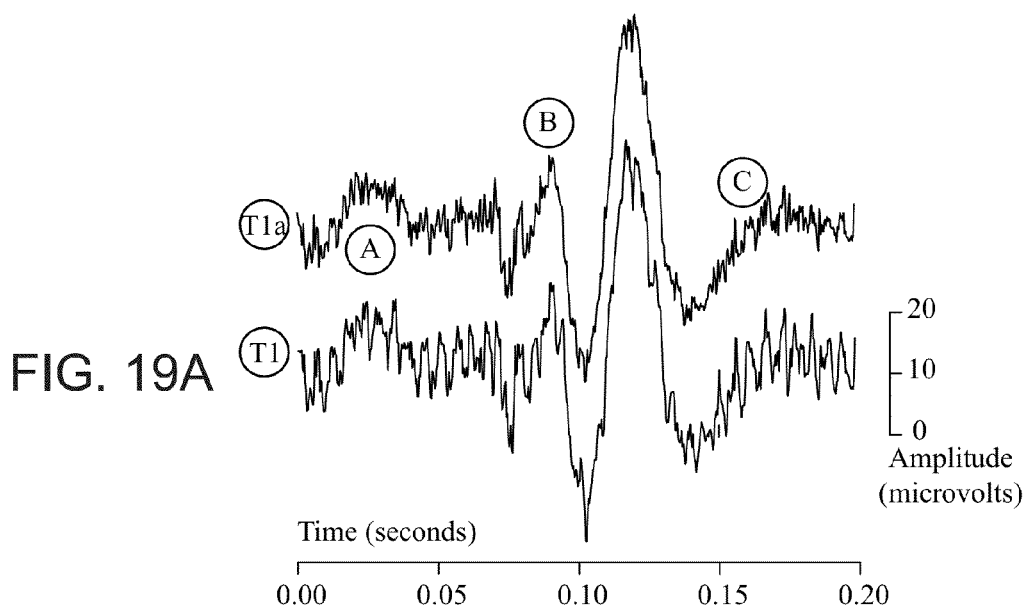
FIGS. 19A-19C show sample recordings of brain electrical potentials from two recording electrodes.
Figure 19B:
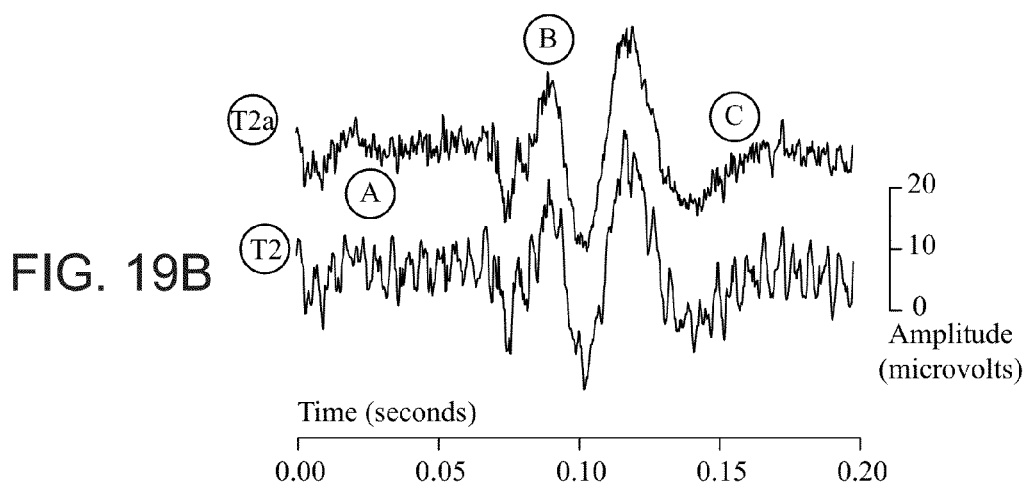
Figure 19C:
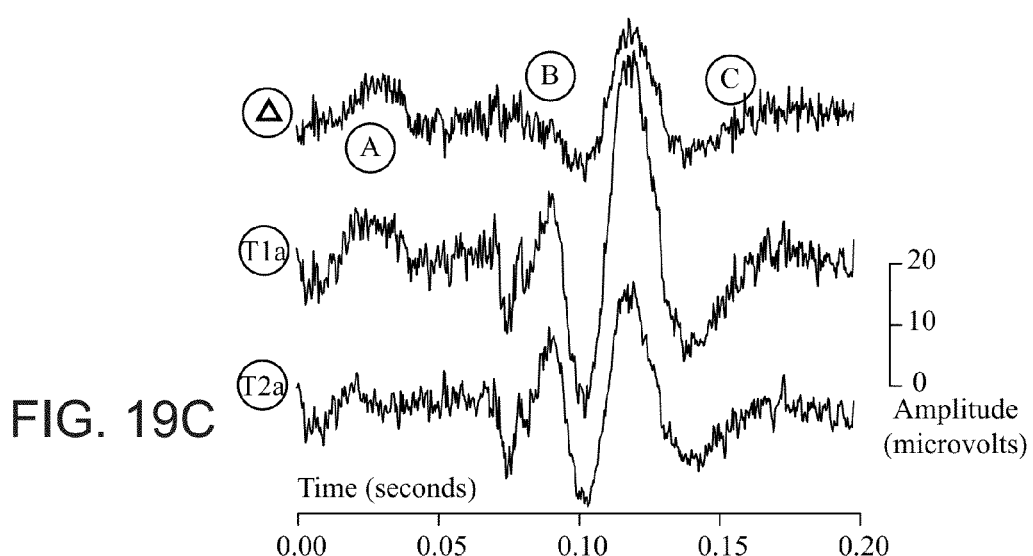

FIGS. 19A-19C demonstrate that the lead can record field potentials, and that different recording sites record different potentials. The recording was obtained from the same lead illustrated in FIG. 16 as discussed above, and with the same placement. The response was evoked by sensory stimulation of the visual pathways by waving a flashlight before the eyes. In FIG. 19A, Trace T1 was recorded from recording site 38, and in FIG. 19B trace T2 was recorded from recording site 39. Spectrum analysis of these traces revealed oscillations at 180 Hz, and 300 Hz, which are believed to result from unintended coupling to the power grid. A Christiano-Fitzgerald filter was applied to remove signal energy near these frequencies, and the filtered traces are denoted T1a and T2a as shown in FIGS. 19A-19C. The trace .DELTA. in FIG. 19C is the arithmetic difference T1a-T2a. The traces look similar, but they are not proportional, as they would be if they resulted principally from electrical cross-talk. At position A, T1/T1a has a more sustained positivity compared to T2/T2a. At position B, the positivity in traces T1/T1a and T2/T2a are nearly identical. The amplitude of the triphasic wave between positions B and C differs considerably in traces T1/T1a and T2/T2a. The amplitude of this recorded potential is somewhat less than the amplitude of an optimally recorded field potential, reflecting the position of the lead near but not in the optic tract.

Figure 20A:
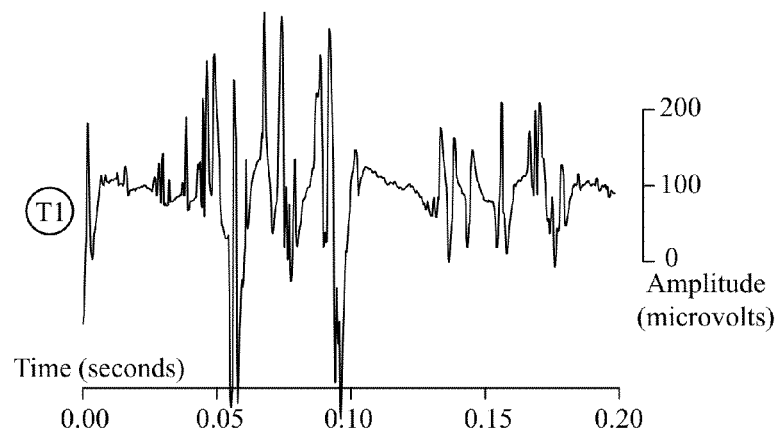
FIGS. 20A-20C show additional sample recordings of brain electrical potentials from two recording electrodes.
Figure 20B:
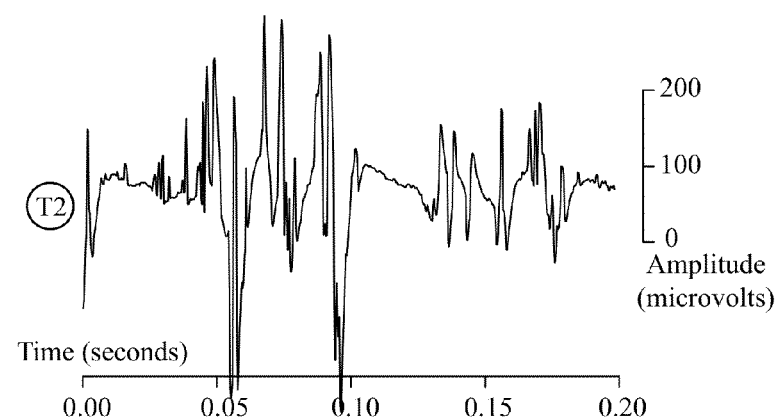
Figure 20C:
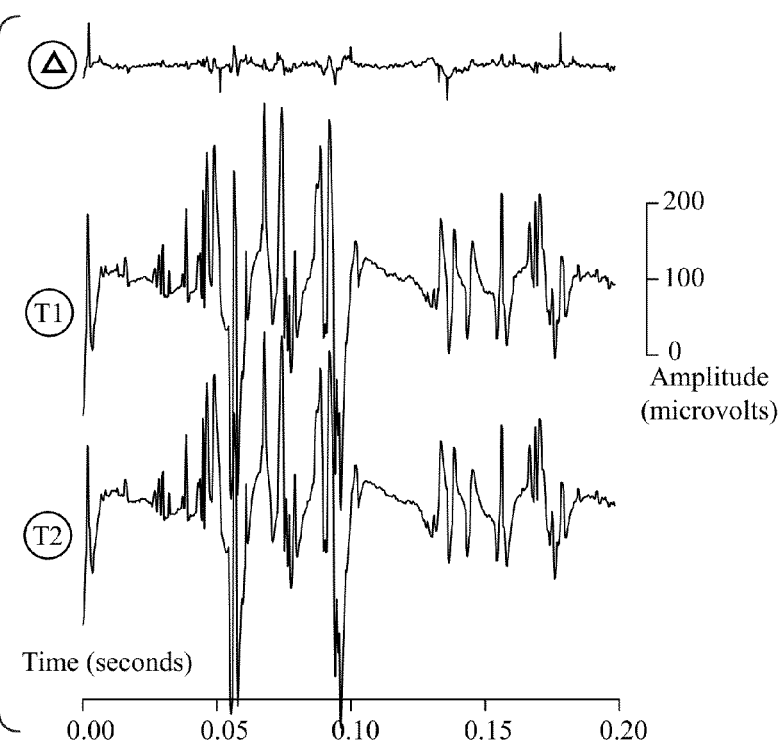

FIGS. 20A-20C demonstrate that the lead can record spontaneous activity field potentials characteristic of placement in a grey matter nucleus. The recording was obtained from a location 3 mm dorsal to the location from which the recording in FIGS. 18A-18C was obtained. Because the amplitude of this recording was much greater than the amplitude of interference from the power grid, Christiano-Fitzgerald filtering was not necessary. Trace T1 in FIG. 20A was recorded from recording site 38, and trace T2 in FIG. 19B was recorded from recording site 39. The trace .DELTA. in FIG. 20C is the arithmetic difference T1-T2. The traces look similar, with a time course and amplitude characteristic of field potential recordings. The difference trace, .DELTA., has several transient waves with duration from 0.5 to 3.5 msec, and amplitude of a few tens of millivolts, characteristic of action potential waveforms. Together with recordings shown in FIGS. 19A-19C, these data demonstrate that a lead such as that illustrated in FIG. 17 can record field potentials from white matter and grey matter, and with suitable signal processing can also record action potential spikes.

TABLE 5

| Activated Surfaces | Stiluation (V) | Ipsilateral Facial Muscle Response Grade | Contralateral Facial Muscle Response Grade |
| --- | --- | --- | --- |
| 36a, 36b, 36c | 1.0 | NR | NR |
| | 2.0 | NR | NR |
| | 2.2 | THR | NR |
| | 2.6 | 1 | NR |
| | 2.7 | 1 | THR |
| 36a | 1.0 | NR | NR |
| | 2.0 | NR | NR |
| | 3.0 | NR | NR |
| | 3.6 | THR | NR |
| | 4.0 | 1 | NR |
| | 4.3 | 1 | NR |
| | 4.5 | 2 | THR |
| .36b | 1.0 | NR | NR |
| | 2.0 | NR | NR |
| | 2.4 | THR | THR |
| | 4.0 | 2 | 2 |
| 36c | 1.0 | NR | NR |
| | 2.0 | NR | NR |
| | 3.0 | NR | NR |
| | 3.5 | NR | THR |
| | 4.0 | THR | 1 |
| | 4.5 | 1 | 1 |
| | 5.0 | 2 | 2 |

In summary, embodiments of the invention, placed at a fixed location within a tissue, can generate a diversity of therapeutic effects and side effects depending upon the magnitude, the time course and the steering of current within the tissue. Steering may be accomplished by at least two basic modes. A first mode is a digital mode, or steering by selection, in which one or a group of electrodes are energized in coordination. The effects within the tissue changing depending upon which electrodes are energized such electrodes connected to a common source of electrical energy, or to a plurality of sources sharing a common electrode remote from the medical lead, such as the metal housing of a programmable pulse generator. A second mode is a bipolar mode, in which a plurality of current sources are connected to electrodes on the lead. By selectively apportioning the total current among the sources, current may be steered to a particular orientation relative to the lead. Unique to preferred embodiments of this invention and its preceding disclosure, three current sources may communicate with three electrodes, so that the current can be oriented in any direction orthogonal to the plane of the long axis of the lead, by selecting a particular pair of current sources and energizing them in coordination with a specific ratio of current magnitude.

The two modes of current steering supported by embodiments of the invention can enable stimulation in such a way as to support obtaining a therapeutic effect, without accompanying side effects. Therapeutic stimulation of the subthalamic nucleus (STN) for the treatment and mitigation of symptoms of Parkinson's disease is limited by the accompanying side effects, such as dysarthria, tonic muscle contraction, paresthesias, eye deviation, and autonomic effects. An example of such treatment is to implant a device common in the art, such as the Medtronic 3389 lead, so that its electrodes are in communication with the dorsal aspect of the STN. This device is comprised of an elongate lead, 1.27 mm in diameter, with four stimulating electrodes disposed near the distal end of the lead, each electrode fixedly attached to the lead, and each electrode fully circumscribing the lead. In the conventional case of monopolar stimulation, in which high frequency stimulus pulses are applied to the electrodes and the housing of the pulse generator serves as the electrical reference. In this example, stimulation of a magnitude sufficient to generate a therapeutic effect spreads clinically significant stimulating current 2 to 3 mm in all directions around the electrode. Spread of the current laterally can lead to stimulation of fibers in the internal capsule, which can lead to conjugate eye deviation, perhaps by directly stimulating axons of the frontal eye fields, and also to dystonia, perhaps by stimulating axons of the medial lemniscus.

Employing a digital mode of current steering mitigates such side effects by moving the source of electric current away from the axons involved in producing the unwanted side effects.

Selectively stimulating electrodes disposed at different angular positions about the elongate axis of the lead moves the center of the field of stimulation by a distance on the order of r {square root over (2(1−cos .theta.>)}, where r is the radius of the lead, and .theta. is the change in angular position along the surface of the lead at a fixed axial position. Based on such reasoning, and the representative dimensions of 1.27 mm for the lead diameter and 2-3 mm for the spread of clinically significant stimulating current, embodiments of this invention can shift the locus of electrical stimulation on the order of 10% to 30% of the stimulation field size. Such a shift may enhance the therapeutic effect, and/or decrease side effects. It permits a greater stimulus magnitude to be employed to generate a therapeutic effect while not increasing side effects. In the particular case under consideration, a field of stimulation in the vicinity of the STN can generate side effects associated with stimulating axons in the internal capsule. By choosing to stimulate electrodes eccentrically positioned on the lead, centered about a more medial anatomical position, instead of an electrode or collection of electrodes completely circumscribing the lead, the zone of effective electrical current is moved medially, away from the fibers of the internal capsule, more into the center of the tissue domain associated with a therapeutic effect. Stimulating the internal capsule would then require a greater stimulus magnitude to be applied to the selected electrode or selected electrode ensemble.

Employing a bipolar mode of current steering mitigates such side effects by generating a flow of current elongated in a preferred direction angular direction about the lead. Contrast this to apparatus common in the art. Such leads can stimulate electrodes near the distal end of the lead, but at different axial positions with opposite polarity to generate a stimulating current field. The shape of the clinically significant current field is elongated in directions parallel to the long axis of the lead, and distributed symmetrically about the lead. In embodiments of the present invention, steering by bipolar stimulation can elongate the field of stimulating current in any chosen direction orthogonal to the long axis of the lead. For the example of treating Parkinson's disease, some placements of a lead require tuning stimulation parameters in order to obtain a favorable balance between therapeutic effects of stimulating the STN and the side effects of generating eye displacements by stimulating fibers in the internal capsule. Embodiments of the present invention can support such a balance by elongating the field of stimulating electrical current along a substantially anterior-posterior axis. This orients the field of stimulation along an axis substantially parallel to the boundary between the STN and the internal capsule, and extends it within the superficial portion of the STN, rather than extending it into deeper portions of the STN. The superficial portion of the STN is the domain most associated with therapeutic effects. Stimulation of deeper portions of the STN may lead to side effects related to modulating the behavior of the autonomic nervous system.

Another embodiment of the invention is illustrated in FIG. 21A. Stimulating sites 136a, 136b, 136c and recording sites 139 are deployed near distal tip 32 of the lead. In this figure stimulating site 136c is obscured from view, but completes an ensemble of three stimulation sites, concentric about the long axis of the lead. Site 136c may be seen in FIG. 29B. Each of the stimulating sites is comprised of two domains—one domain distal to the recording site 139, and another domain proximal to the recording site 139. The two domains are electrically continuous inside, so that they function together as a single electrode, in the sense that a potential cannot be applied to one portion of the electrode without also applying the potential to all other portions of the electrode. Electrical conductors 50, 60 communicate with the stimulating electrodes and recording electrodes, and course through a flexible body 10. In a preferred embodiment, electrical conductors 50 and 60 are coated with an insulating film, such as polyimide or parylene, except in the vicinity of their electrical contact with their respective electrodes at the distal end, and the electrical connector at the proximal end. In this embodiment, the conductors form a helical path about a tube 72 surrounding a central lumen, which can accommodate a stylet 91. The tube 72 may be made of a biocompatible polymer such as PEEK, PTFE, polyurethane, polyethelyne, Santoprene™ or a silicone elastomer. In other embodiments the tube 72 need not be present, and the wall of the lumen and the outer surface of the flexible lead may be formed as a single part. The outer surface of the flexible lead 10 and tip 32 may be composed of a biocompatible material. It may be formed by a process such as overmolding about the other structural elements. The tip 32 and body 10 may be formed of different materials, and the tip 32 may incorporate additional structural elements, such as ports, pores or valves which selectively or nonselectively permit or facilitate exchange of matter between the lumen of the probe and the tissue in the vicinity of the tip.

FIG. 21B illustrates a view of the embodiment introduced in the preceding paragraph in which a segment of the distal end of the probe has been removed in order to show some internal structure. The removed section is bounded by radial semiplanes extending from the long axis of the probe through the insulating material between stimulation sites 136a and 136c, and between stimulation sites 136a and 136b. An additional cut is made between those planes, and orthogonal to them, at an axial position near the most proximal end of the stimulation sites. It shows the insulating material of the probe body 10 extending about and between the stimulation sites 136a, 136b, 136c, and the recording site 139. It also shows a connection between an electrical conductor 60 and the recording site 139, which traverses internal to the surface of the lead body 10 and adjacent to the stimulation sites. An interior face of proximal end of stimulation site 136a is shown.

FIG. 21C extends the view of the internal structure introduced in FIG. 21B by removing the insulating material of the probe body 10 and the tip 32. With most of stimulation site 136a removed, the remaining two stimulation sites in the concentric ensemble 136b and 136c are clearly visible. The internal structures connecting the proximal and distal domains of the electrodes 136b and 136c are enumerated as 146b and 146c. They course internally to the recording electrodes 139 and are concentric with it. Additionally, a connection between the proximal end of stimulating site 136a, enumerated as 148a, and an electrical conductor 50 is seen in this view. This view is rotated in FIG. 21D, to show the surfaces of stimulation sites 136b and 136c which is in communication with the target tissue in the complete implanted assembly.

Figure 22A:
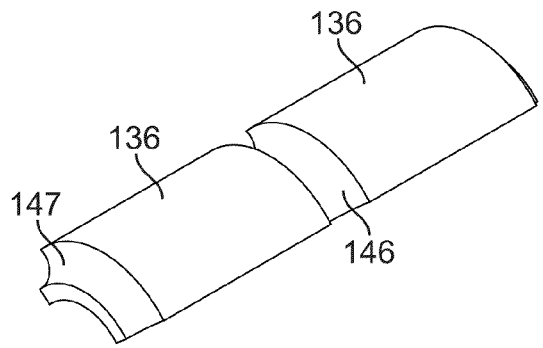
FIGS. 22A-22C illustrate a stimulating electrode with an internal connection structured to allow favorable placement of an electrode suitable for recording local tissue potentials.
Figure 22B:
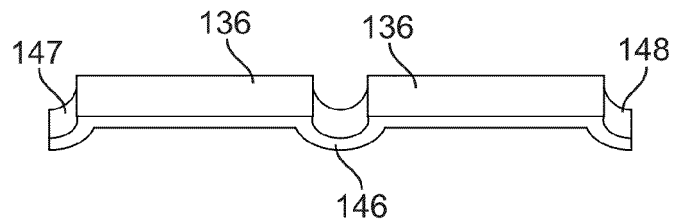
Figure 22C:
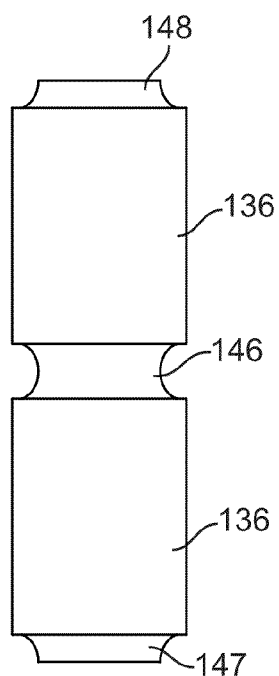

FIGS. 22A-22C illustrate three views of the embodiment of the stimulation sites shown in FIGS. 21A-21D. A perspective view is shown in FIG. 22A, a side view is shown in FIG. 22B and a top view is shown in FIG. 22C. The exposed proximal and distal stimulating surfaces 136 are shown, with their internal communicating segment or connector 146. The external surface of the proximal internal section 148 provides a point of attachment for electrical conductors 50 (not shown in this figure). The distal internal section 147 need not be present in alternative embodiments, but may be advantageous in the manufacturing process, as a point of attachment for accessory structures, or as surface which helps to secure overmolded polymer to the probe. Additional internal structure, such as a fenestration of the internal section 147, may further aid in securing overmolded polymer, or flow of such polymer around the other internal components.

Such a structure such as that illustrated in FIGS. 22A-22C may be formed by procedures familiar to those skilled in the art, such as stamping sheet of metal. An alternative procedure of forming such a structure is to crimp a metal tube to form impressions of the shape of 146 at the positions of features 146, 147 and 148, and further cutting across the crimped tube through sections 147 and 148, and cutting axially to form the completed shape. In alternative embodiments, the electrodes may be formed using thin-film or flexible printed circuit technology. The three dimensional structure may be formed directly, or by wrapping a flexible printed circuit into an elongated cylinder. Such embodiments all comprise the essential structure of an ensemble of three concentric stimulation sites, together encircling the elongate axis of the probe, each comprised of electrically connected proximal and distal domains, with the proximal domains located at a axial position common to each other, and the distal domains located at an axial position common to each other, and with a recording surface located at an axial position between the proximal and distal domains, with each stimulating and recording electrode communicating with both the target tissue and exactly one electrical conductor extending proximally to an electrical connector or controller unit.

Figure 23A:
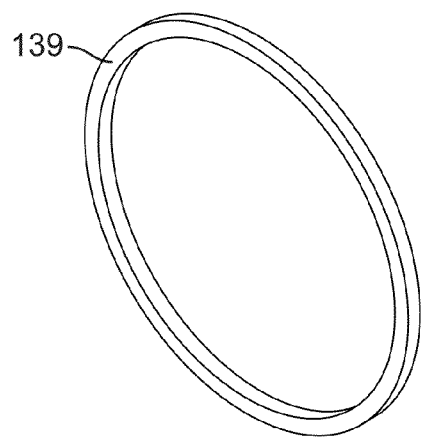
FIGS. 23A-23C illustrate embodiments of an electrode suitable for recording local tissue potentials.
Figure 23B:
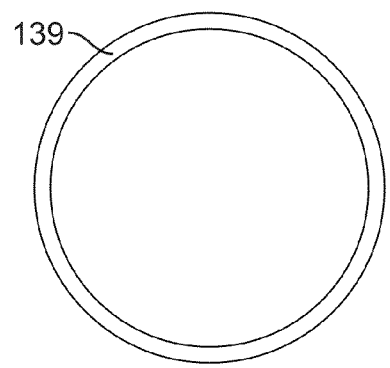
Figure 23C:
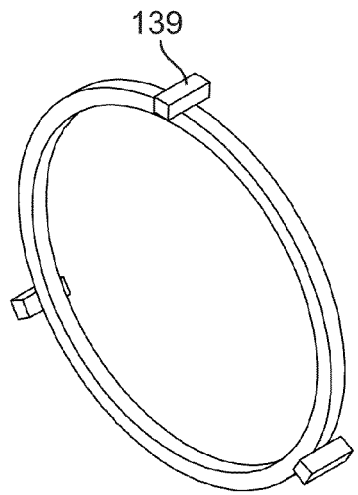

FIGS. 23A-23C illustrate an embodiment of a recording electrode 139 encircling the long axis of the probe. FIG. 23A shows a perspective view, and FIG. 23B shows a front view, in a plane orthogonal to the long axis of the probe. The electrical potential of this embodiment of the recording electrode is determined by the potential of the target tissue in the near vicinity of the electrode, averaged across all angular positions about the long axis of the probe. In alternative embodiments, the exposed recording surface may be more limited, and may be a multiply connected surface in a topological sense, in order that the recording electrode potential represents a more spatially restricted average. Such a restricted average is more amenable to signal processing methods which incorporate assumptions in order to model such an average potential signal as a particular average of a particular ensemble of sub-signals. FIG. 23C illustrates a perspective view of an exemplary embodiment of a recording electrode adapted to record such a restricted average potential. In this embodiment, three raised recording surfaces communicate with a cylinder or ring internal to the probe.

A structure such as that illustrated in FIG. 23A and FIG. 23B can be formed by welding or fusing two ends of a wire, to form a circular loop of the required diameter. Such wire could have a rectangular or square profile, as depicted in FIG. 23A, or have a circular or other advantageous profile. Alternatively, such a structure could be formed by cutting a tube to release a circular profile. In alternative embodiments, the electrodes may be formed using thin-film or flexible printed circuit technology. The three dimensional structure may be formed directly, or by wrapping a flexible printed circuit into an elongated cylinder, and may be formed in coordination with the stimulating electrodes 136a, 136b, 136c, and/or the communicating conductors 50, 60.

The embodiments of the invention illustrated in FIGS. 21A-23C possess structure which expediently supports specifically targeted brain stimulation, compared to structures employing an unconstrained multiplicity of conductive surfaces. Such embodiments often have four electrodes. Four electrodes can communicate with a controller through four conductors, and can be fabricated to interface with 4 channel pulse generators and controllers known to those skilled in the art. Such embodiments can connect to such controllers and pulse generators through connectors known to those skilled in the art, such as the IS4 connector. Not only does encircling the elongate axis of the probe with three concentric stimulating electrodes support an efficient method of steering the field of electrical stimulation in a plane orthogonal to the elongate axis, it enables deployment of an additional electrode specialized for recording tissue potentials, while simultaneously interfacing to lead extensions, pulse generators, connectors, controller, and amplifiers known to those skilled in the art. In these embodiments, the recording electrode is placed at the axial position best suited to record tissue potentials most representative of that portion of the stimulation field nearest the probe.

Exemplary embodiments of the present invention support orienting the current about the lead parallel to any direction in a plane orthogonal to the elongate axis of the lead, and also allows for a recording electrode specialized for recording local tissue potentials. In contrast, embodiments with four electrodes encircling the lead and concentric with the long axis of the lead can support orienting current about the lead parallel to any direction in a plane orthogonal to the elongate axis of the lead, but some sacrifice must be made in order to afford recording ability while still retaining compatibility with industry standard interfaces. Recordings must be obtained from one of the stimulating electrodes, optimized for facilitating transfer of current to the tissue (relatively large surface area), rather than for recording local potentials (relatively small surface area). The electronic circuitry required to record low level signals from electrodes which are simultaneously stimulating is quite complex, because the recording circuits must possess a very high dynamic range, the stimulating currents must be very precisely known or very precisely controlled, and the interaction between stimulating and recording circuits must be very precisely known and accounted for. If one electrode, or a pair of electrodes is dedicated for recording, then the magnitude of the dipole generating a stimulation field is restricted, because only half of the electrodes can contribute to stimulation, and the number of directions in which a stimulation field can be generated is likewise restricted. Embodiments of the present invention obviate these disadvantages by supporting efficient orientation of the stimulation field with electrodes of surface area sufficiently large for clinically efficacious electrical stimulation. They independently support targeted recording through an additional electrode, or additional electrodes, with a small surface area suitable for positioning recording surfaces near the target tissue. Because the recording electrodes are small, using such an electrode for recording does not have the side effect of displacing stimulating electrodes further from the target tissue. In contrast, leads which employ stimulating electrodes as recording electrodes may require stimulating current to pass through electrodes which are not advantageously placed. Embodiments which employ three stimulating electrodes and one recording electrode achieve these objectives, while simultaneously conforming to the constraints of industry standard interfaces.

Figure 24:
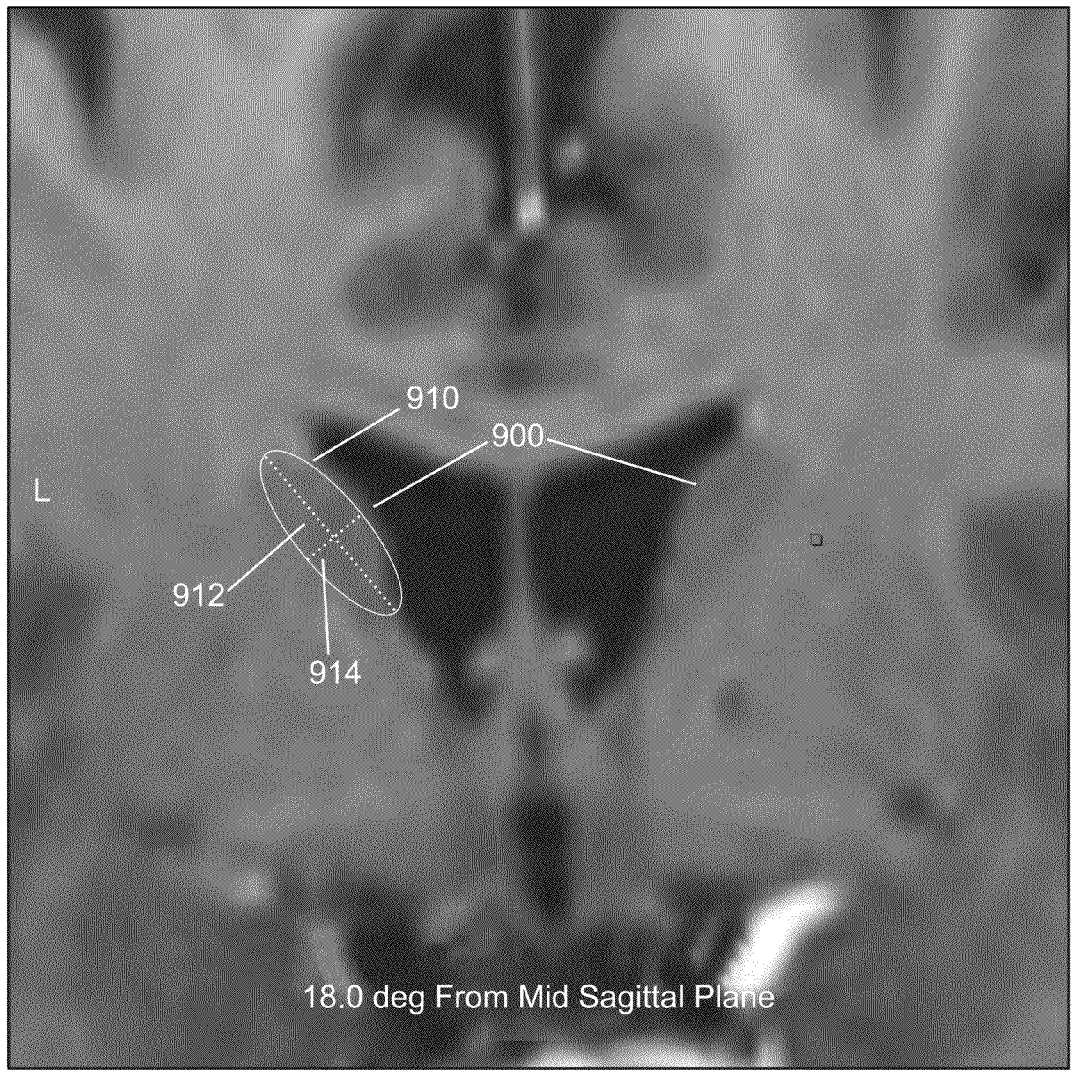
FIG. 24 shows an example of a locus of neurons in the caudate nucleus, modulation of which can engender favorable therapeutic effects upon phantom perceptions, such as tinnitus and visual hallucinations.

FIG. 24 shows an MRI image of a coronal section of the brain, with an ellipse 910 substantially circumscribing the caudate nucleus 900. U.S. Patent Publication No. 2010/0198281 discloses stimulation of the caudate nucleus, and is incorporated herein by reference. Stimulation of the caudate nucleus may be used to treat tinnitus and other phantom perceptions, with stimulation loci defined by cortico-striatal relationships, for example, the caudate nucleus domain receiving projections from auditory-related cortical areas can be stimulated to treat tinnitus. Other patent and scientific literature report that in a primate animal model, the auditory cortices tend to project most strongly to the ventromedial portions of the head of the caudate nucleus and the rostral putamen and to the medial portion of the tail. Extrastriate corticostriatal connections are directed mainly to the dorsal portion of the head and the body of the caudate nucleus, to the genu, and to the lateral portion of the tail. To the extent that the human anatomy parallels the anatomy of the animal model, the ventro-medial quadrant of ellipse 910, is an example of a stimulation target for treating auditory phantom perceptions, including tinnitus, whereas the dorso-lateral quadrant of the ellipse 910 is an example of a stimulation target for treating visual phantom perceptions. Embodiments of the present invention targeted for treating tinnitus and other phantom perceptions employ stimulating electrodes with an elongated aspect ratio in order to stimulate a sufficiently large volume of tissue in the caudate nucleus. Embodiments of the present invention that support practice of the treatment are enhanced by directing the field of stimulation into the caudate domain associated with a particular therapeutic effect, and away from neighboring regions, and by simultaneously placing one or more recording electrodes in contact with the target of therapeutic stimulation, and also in contact with tissues which, if stimulated, could potentially be associated with side effects. Embodiments of the present invention for which the overall axial extent of connected stimulating surfaces is ⅓ to 1 times the length of the major axis 912 of the ellipse 910 are of a suitable size to direct a targeted field of clinically efficacious stimulation in the practice of the method. Table 6 presents example measurements of the major axis 912 and minor axis 914 of the ellipse, based upon images obtained from 18 patients. The arithmetic mean length of the major axis of the ellipse in this series is 12.8 mm. A preferred embodiment of the present invention intended to support the practice of the treatment of tinnitus and other phantom methods would have a lead diameter of 1.27 mm, three electrodes in each stimulating ring, each subtending an arc of 111 degrees and an arc length of 1.2 mm, with three interposed insulating regions, each subtending an arc of 9 degrees and an arc length of 0.1 mm. In such preferred embodiments, the collective axial extent of the internally axially connected electrodes ranges from 4.25 to 12.8 mm. This corresponds to an aspect ratio of 3.5:1 to 10.4:1, based upon the arc length and the overall length of the internally axially connected stimulating electrodes. In embodiments in which four electrodes, each subtending an arc of 81 degrees about the lead and an arc length of 0.9 mm, with interposed insulating region is each subtending an arc of 9 degrees with an arc length of 0.1 mm, the corresponding aspect ratio is 4.7:1 to 14.3:1, based upon the arc length and the overall length of the internally axially connected stimulating electrodes. Other embodiments of the invention could have a larger or smaller lead diameter, with an anticipated range of 0.635 to 2.54 mm. With this range of lead diameters, the range of collective aspect ratios for embodiments with three electrodes circumscribing the lead is from 1.7:1 to 20.8:1. The range of collective aspect ratios for embodiments with four electrodes circumscribing the lead is 2.3:1 to 28.5:1.

TABLE 6

| | Measurement of ellipse axes in mm. | |
|---|---|---|
| | Major Axis (912) | Minor Axis (914) |
| | 14.5 | 5.4 |
| | 10.5 | 3.9 |
| | 16.4 | 5.6 |
| | 13.4 | 4.2 |
| | 11.2 | 5 |
| | 12.9 | 4.1 |
| | 10.4 | 4.8 |
| | 10.8 | 4.4 |
| | 14.7 | 6.1 |
| | 13.4 | 5.4 |
| | 13.8 | 6.2 |
| | 14.1 | 5.4 |
| | 11.4 | 5.2 |
| | 10.6 | 3.8 |
| | 13.1 | 5.5 |
| | 15.1 | 5.8 |
| | 10.6 | 4.6 |
| | 13 | 5.1 |
| Mean | 12.77 | 5.03 |
| Sample Std. Dev. | 1.84 | 0.73 |

Figure 29A:
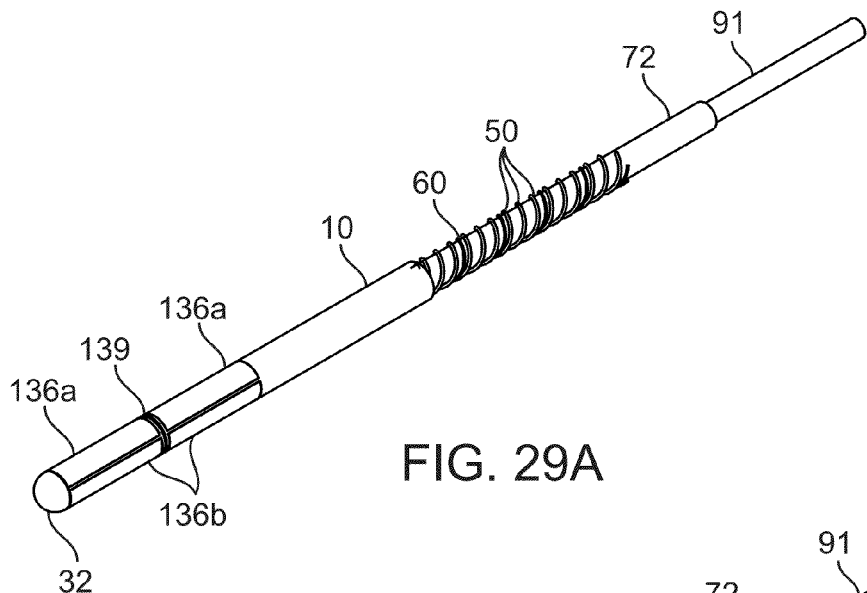
FIGS. 29A-29C illustrate an embodiment of a lead, similar to the embodiment of FIG. 17, structured to facilitate independent therapeutic modulation of neighboring portions of a locus of neurons in the caudate nucleus for the treatment of auditory phantom perceptions such as tinnitus and also visual phantoms perceptions and hallucinations.
Figure 29B:
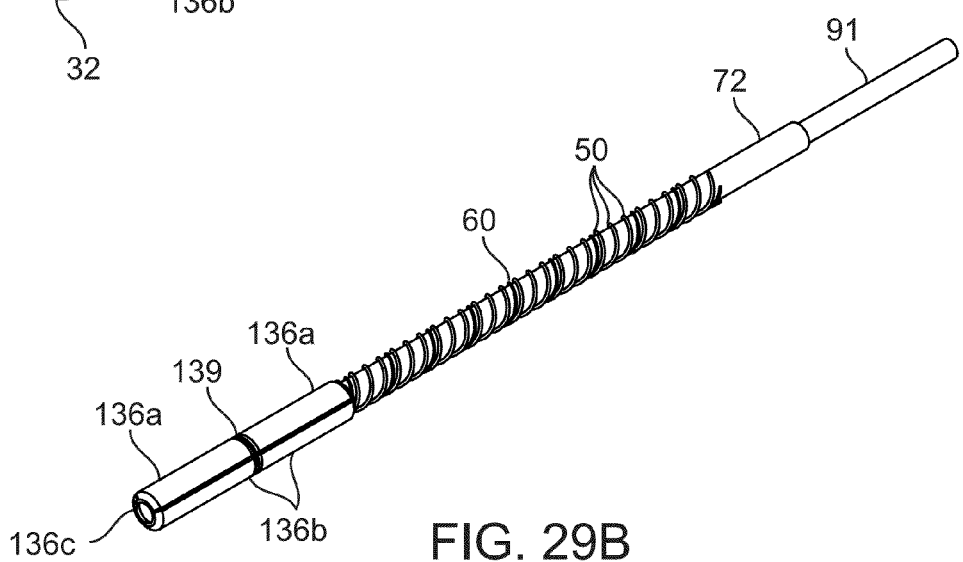
Figure 29C:
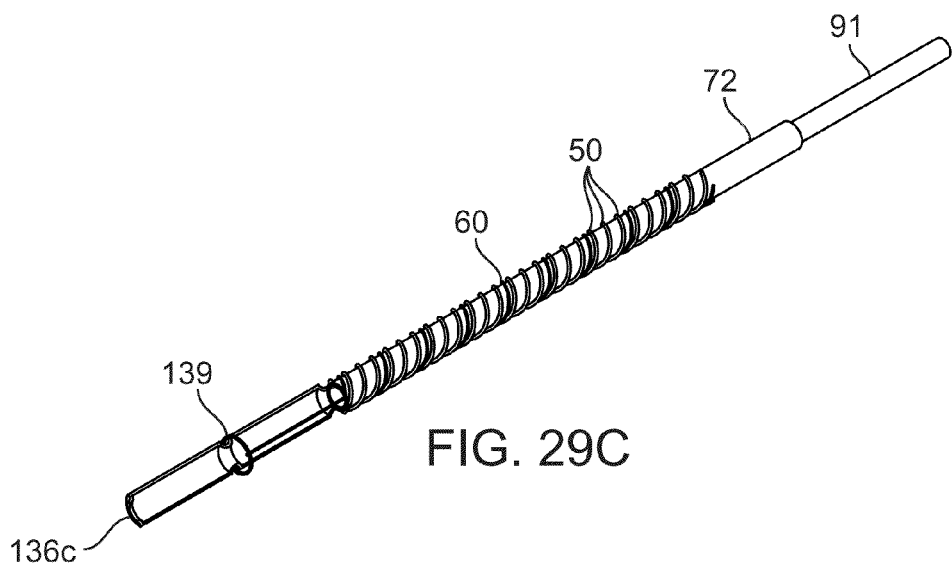
Figure 30A:
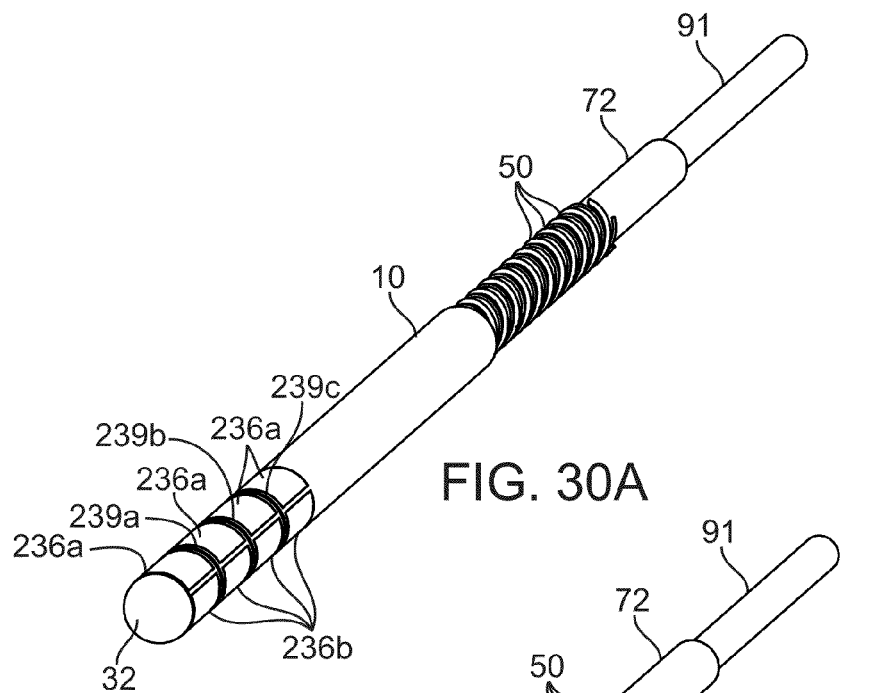
FIGS. 30A-30C illustrate an exemplary embodiment in which structures similar to those illustrated in FIGS. 21A-21D are specialized for the stimulation of a locus of neurons in the caudate nucleus for treatment of auditory or visual phantom perceptions, in which two sets of stimulating and recording electrodes may be independently energized to support independent and coordinated treatment of visual and auditory phantom perceptions.
Figure 30B:
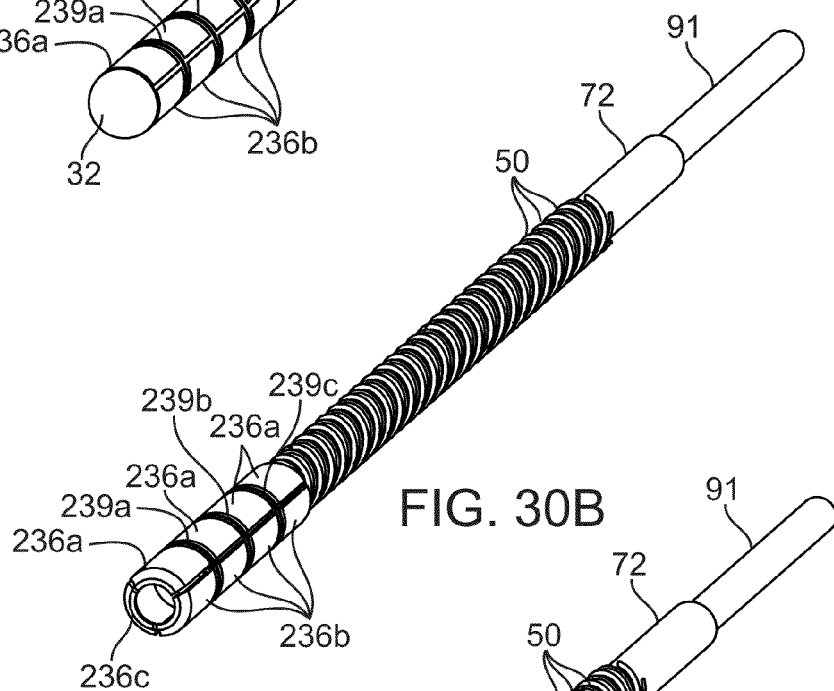
Figure 30C:
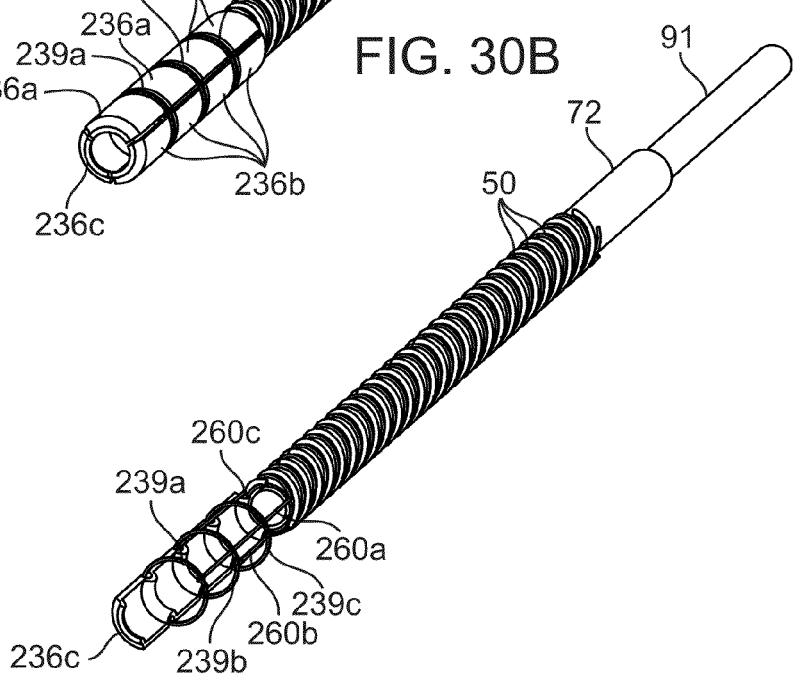

FIGS. 25A-30C illustrate exemplary embodiments of the invention with an aspect ratio within the range appropriate for treating auditory phantoms by electrical stimulation of the ventro-medial quadrant of the ellipse 910 in FIG. 24. FIGS. 25A-28D illustrate embodiments without recording electrodes, while FIGS. 29A-29C illustrate an embodiment with a recording electrode, and FIGS. 30A-30C illustrate an embodiment with 3 recording electrodes. The figures illustrate appropriate aspect ratios in the range discussed in the preceding paragraph.

Figure 25A:
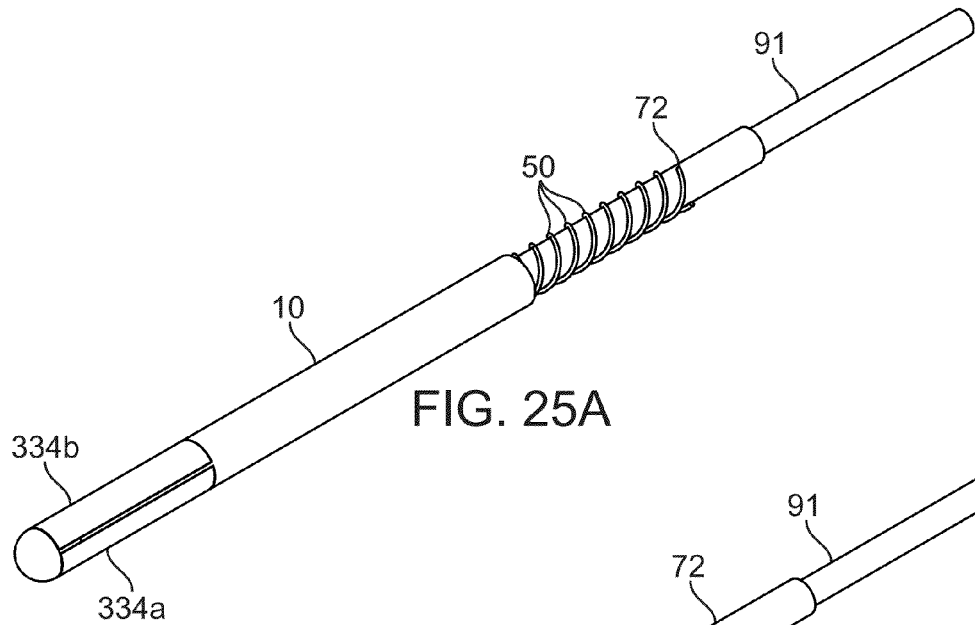
FIGS. 25A-25C illustrate an additional exemplary embodiment, structured to support treatment of phantom perceptions by modulating a locus of neurons in the caudate nucleus, in which three stimulating electrodes circumscribe a medical lead.
Figure 25B:
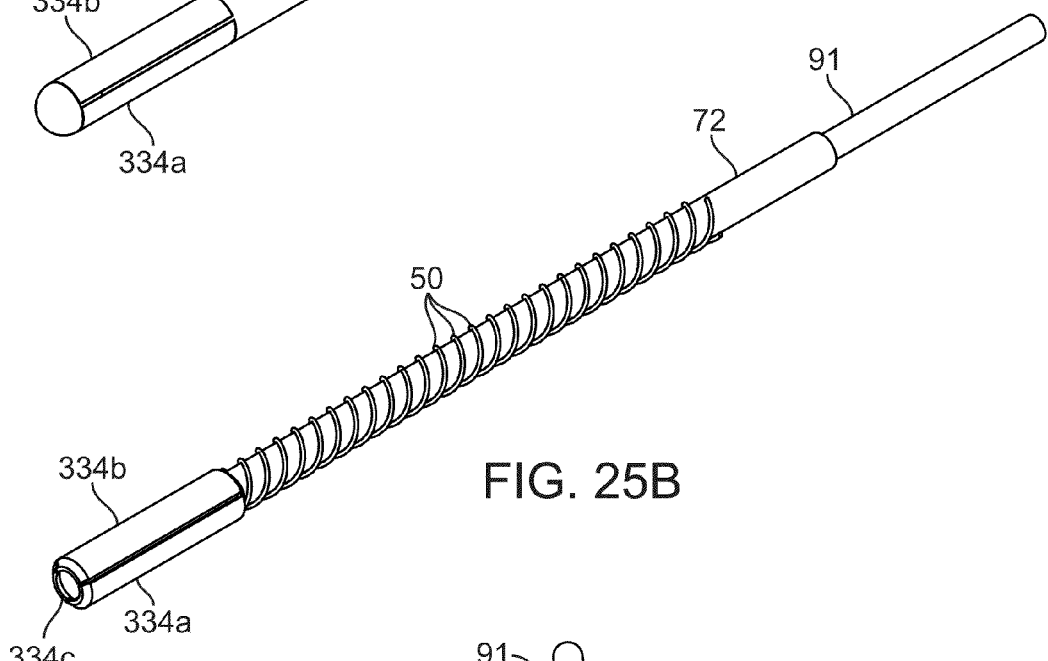
Figure 25C:
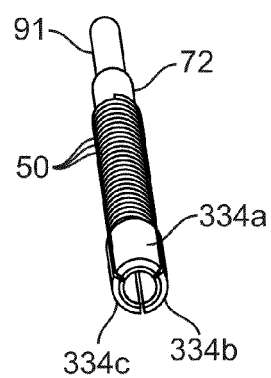
Figure 26A:
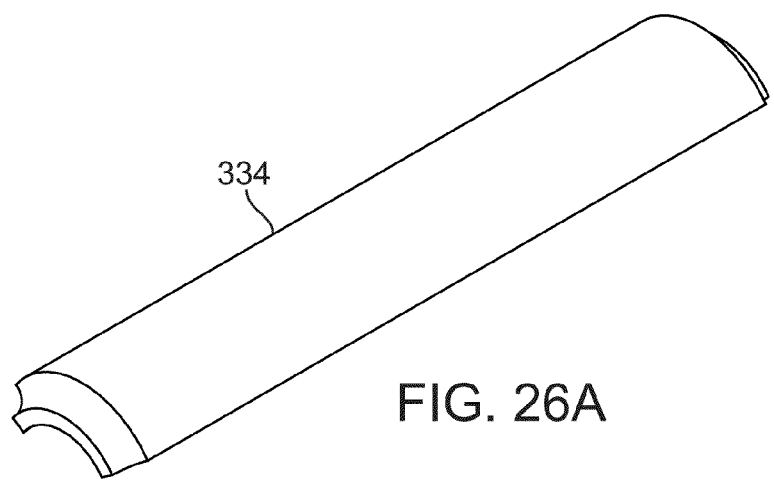
FIGS. 26A-26D illustrate an embodiment of an individual stimulating electrode with structure suitable to serve as a component of a lead such as that illustrated in FIG. 25.
Figure 26B:
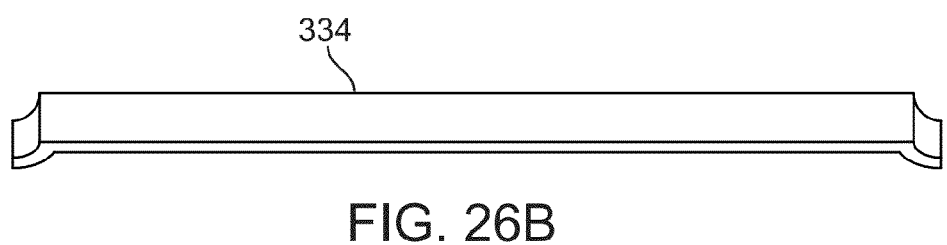
Figure 26C:
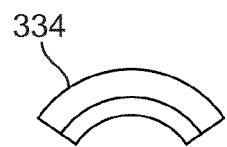
Figure 26D:
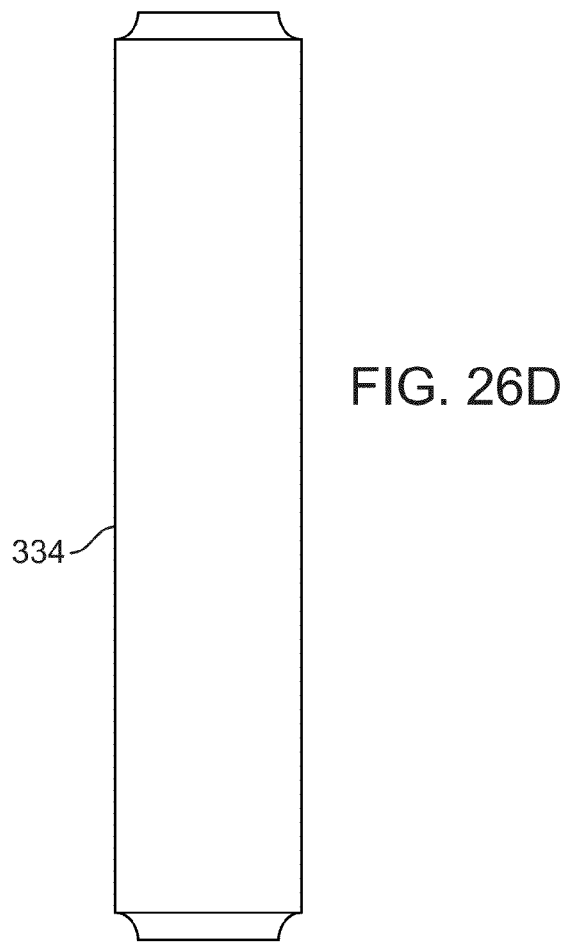

FIGS. 25A-25C illustrate an exemplary embodiment of the invention with three stimulating electrodes 334a, 334b, 334c in an annular stimulating region, and having no recording electrodes. FIGS. 26A-26D further illustrate the stimulating electrodes of this embodiment. This embodiment illustrates an electrode 334 with surface subtending an arc of 111 degrees. Aspect ratio is computed as the ratio of the axial length of the stimulating surface to the arc length along the surface. The aspect ratio of the electrodes illustrated in FIGS. 25A-25C and 26A-26D is near 4.

Figure 27A:
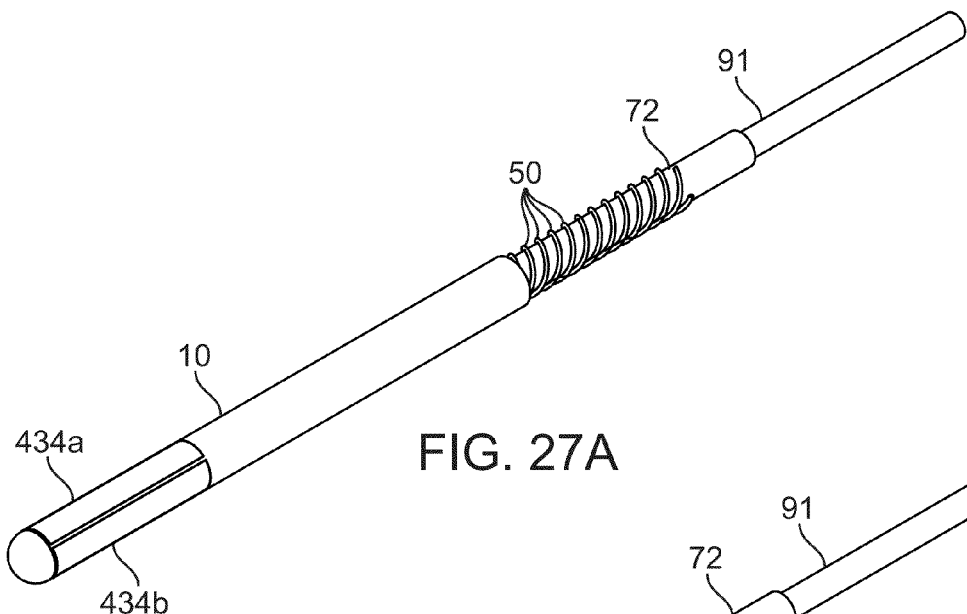
FIGS. 27A-27C illustrate an additional exemplary embodiment, structured to support treatment of phantom perceptions by modulating a locus of neurons in the caudate nucleus, in which four stimulating electrodes circumscribe a medical lead.
Figure 27B:
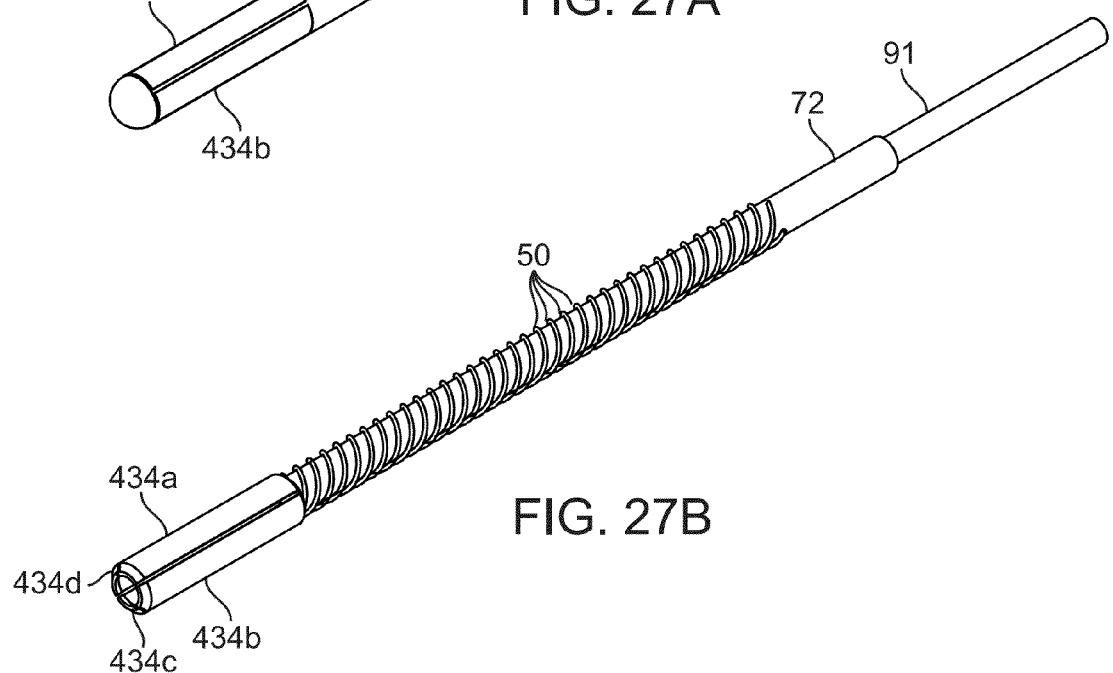
Figure 27C:
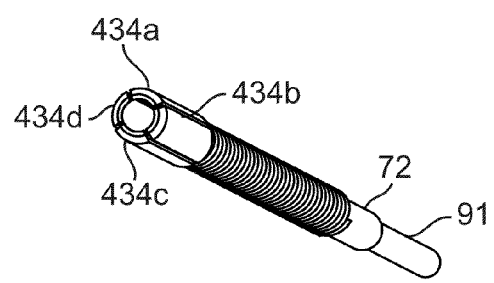

FIGS. 27A-27C illustrate an exemplary embodiment of the invention with four stimulating electrodes 434a, 434b, 434c, 434d, and having no recording electrodes. FIGS. 28A-28D further illustrate the stimulating electrodes of this embodiment. This embodiment illustrates an electrode 434 with surface subtending an arc of 81 degrees. The aspect ratio of the electrodes in this embodiment is near 5.5.

FIGS. 29A-29C illustrate an exemplary embodiment of the invention with three stimulating electrodes 136a-c and a recording electrode 139, similar to the embodiment illustrated in FIGS. 21A-21D, thus a proximal annular stimulating region is electrically coupled with a distal annular stimulating region, and a recording electrode 139 is disposed over the electrical coupling between the two annular stimulating regions. This embodiment illustrates stimulating electrodes 136a-c with an exposed surface subtending an arc of 111 degrees. The axial length used in computing the aspect ratio is the axial extent from the most proximal portion of the dorsal portion of the proximal exposed surface, to the most distal portion of the distal exposed surface. In particular, the axial length of the internal connection is included in the length used for calculating the aspect ratio, in addition to the axial length of the two exposed surfaces, regardless of whether the exposed surfaces and the interconnection are fabricated as a single structure, or as an assembly. The aspect ratio of this embodiment of the invention is near 6.5.

FIGS. 30A-30C and 31A-31D illustrate an embodiment of the invention with three stimulating electrodes 236a-c and three recording electrodes 239a-c. Each of the recording electrodes 239a-c overlays one internal connection of each of the three stimulating electrodes 236a-c. Each stimulating electrode 236a-c has three internal connections along its length. The exposed surfaces of the three stimulating electrodes each subtend an arc of 111 degrees about the long axis of the lead, and are separated by an insulating member subtending the remaining arc. Other embodiments disclosed herein having a plurality of stimulating electrodes formed into an annular stimulating region may also be separated by an insulating member. Each stimulating electrode 236a-c communicates with an individual electrical conductor 50. Each recording electrode 239a-c communicates with an individual electrical conductor 60. FIGS. 31A-31D further illustrate the structure of the electrodes 236. In particular, in this embodiment, the aspect ratio of the electrodes 236 is near 4.

FIGS. 32A-35C illustrate additional exemplary embodiments of the invention, illustrating structure which may employed in combination with other structure described in this disclosure, in order to create further embodiments of the invention.

Figure 32A:
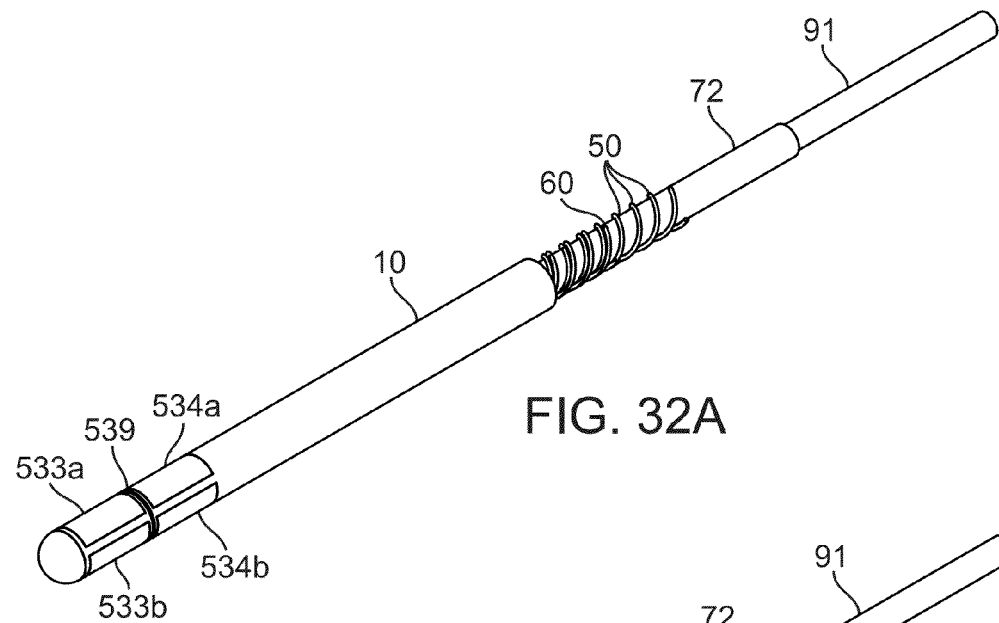
FIGS. 32A-32C illustrate other embodiments of stimulating and recording structures.
Figure 32B:
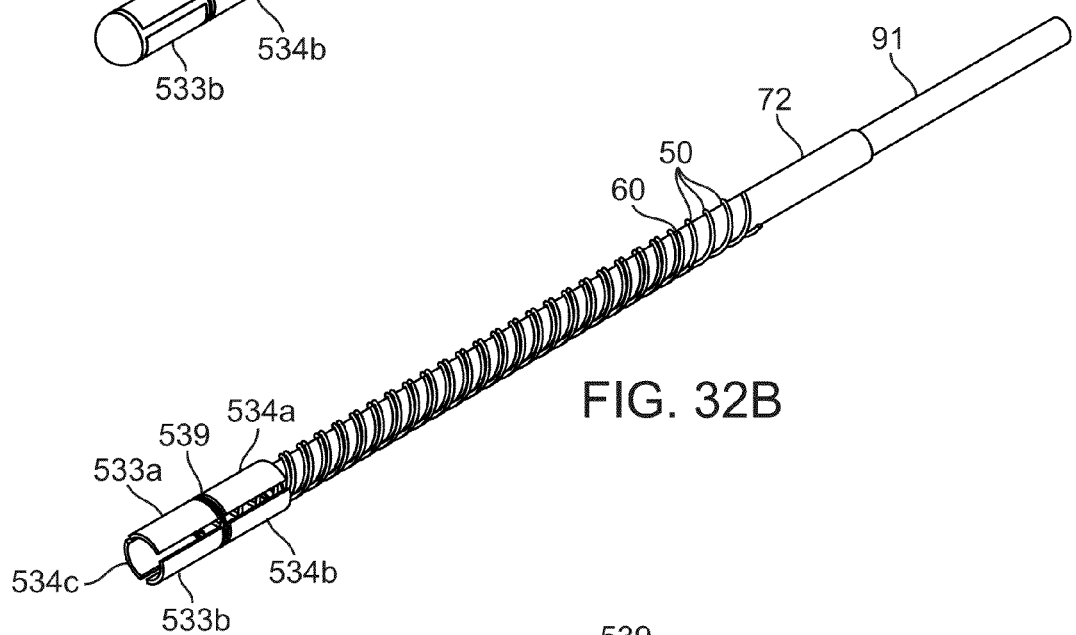
Figure 32C:
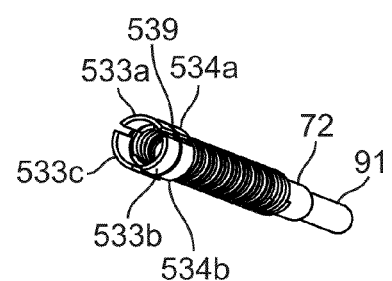

FIGS. 32A-32C illustrate an embodiment of the invention in which two sets of three stimulating electrodes are separated axially, and a recording electrode is interposed between the sets of stimulating electrodes. The more distal set of stimulating electrodes is denoted 533a, 533b, and 533c, and the more proximal set of stimulating electrodes is denoted 534a, 534b and 534c. The stimulating electrodes communicate with electrical conductors 50, which may wrap around a tube 72 defining a lumen. A stylet 91 may be removably placed within the lumen. The recording electrode 539 is disposed between the proximal and distal stimulating electrodes, and is separated from the stimulating electrodes by insulating material which may be continuous with the outer body of the lead 10. The recording electrode communicates with an electrical conductor 60. The conductors 50 and 60 also communicate with a proximal electrical connector, not shown in these figures. The proximal and distal sets of stimulating electrodes are preferably electrically coupled together so that the six total electrodes function as three electrodes when energized. However, one of skill in the art will appreciate that the six total electrodes may also be energized independently of one another, or one set, two sets, or all sets of proximal and distal electrodes may be electrically coupled together.

Figure 33A:
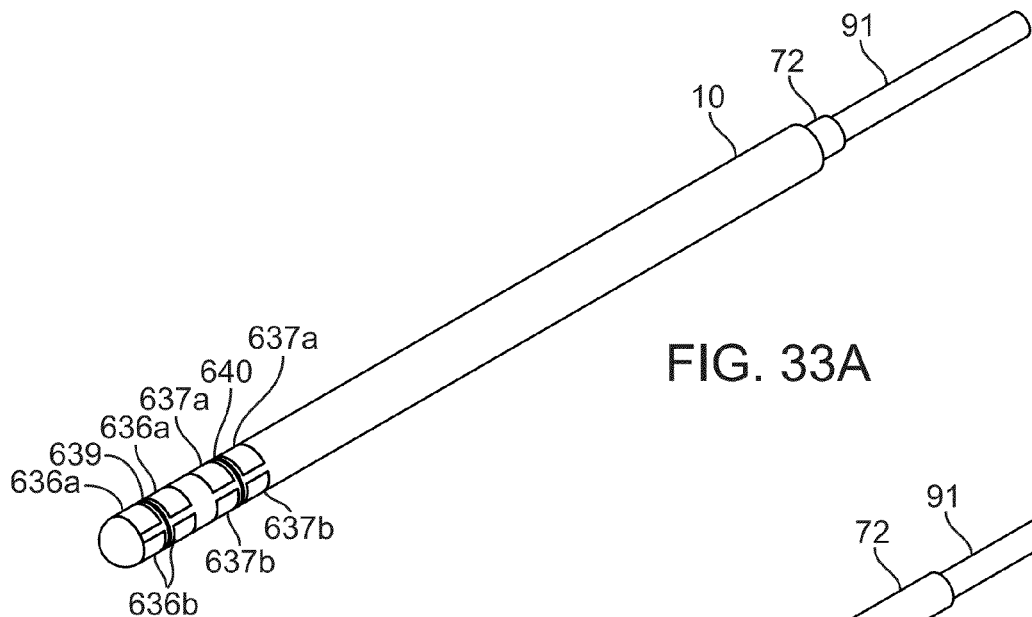
FIGS. 33A-33C illustrate an embodiment of stimulating and recording structures.
Figure 33B:
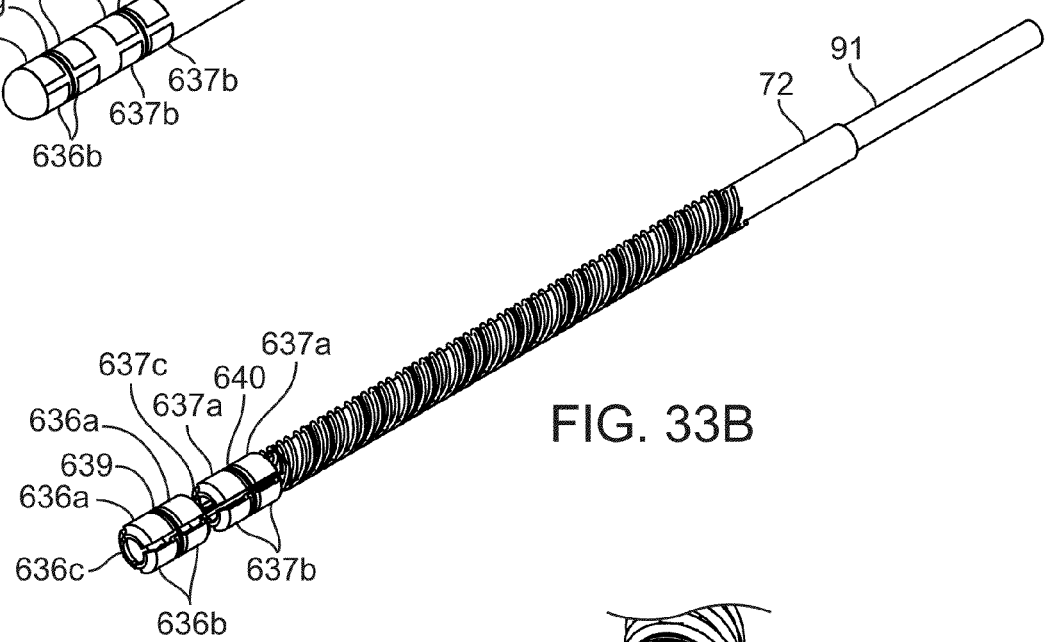
Figure 33C:
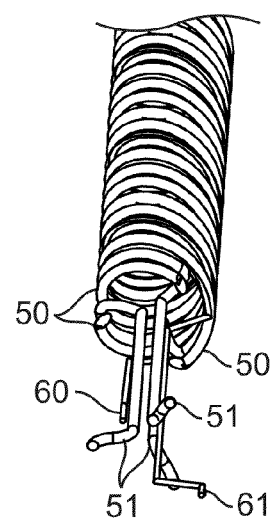

FIGS. 33A-33C illustrate an embodiment of the invention in which two sets of electrodes, each electrode comprised of a proximal and distal domain connected internally within the lead. The distal set of stimulating electrodes is denoted 636a-c, the proximal set of stimulating electrodes is denoted 637a-c. A recording electrode 639 is placed at an axial position within the axial gap separating the proximal and distal domains of the electrodes 636a-c. Another recording electrode 640 is similarly placed at an axial position within the axial extent of the electrodes 637a-c. Other embodiments may also include one or more recording electrodes positioned proximal to the most proximal exposed surfaces of the distal stimulating electrodes 636a-c, and distal to the most distal exposed surfaces of the proximal stimulating electrodes 637a-c. Each of the distal stimulating electrodes 636a-c communicates with an individual electrical conductor 51, and each of the proximal stimulating electrodes 637a-c communicates with an individual electrical conductor 50. The distal recording electrode 639 communicates with an electrical conductor 61, and the proximal recording electrode 640 communicates with an electrical conductor 60. In this embodiment the electrical conductors 50, 51, 60 and 61 are wrapped as a helix about a tube 72, forming the wall of a central lumen. A stylet 91 may be removably placed within the lumen. Such stylet can increase the stiffness and control the shape of the lead during surgical placement. Removing the stylet makes the lead less stiff and more flexible, and more able to deform in coordination with the surrounding tissues.

Embodiments of the invention such as illustrated in FIGS. 33A-33C may be arranged so that the two sets of stimulating electrodes can be deployed in simultaneous proximity to two targets for therapeutic stimulation. An example of two targets for therapeutic stimulation are the tissue within the ventromedial quadrant of the ellipse 900 of FIG. 24, which may be electrically stimulated to treat perception of auditory phantoms such as tinnitus, and the tissue within the dorsolateral quadrant of the ellipse 900, which may be electrically stimulated to treat perception of visual phantoms. Key design choices in creating such an embodiment are the aspect ratio of the electrodes, which is chosen to be on the order of one dimension of each therapeutic target, and the axial separation of the stimulating electrodes, which is chosen to be on the order of the of the separation between the centroids of the therapeutic targets along the direction of the long axis of the lead. Thus, in alternative embodiments, one set of electrodes may have a first aspect ration, while a second set of electrodes may have a second aspect ratio.

Embodiments of the invention such as illustrated in FIGS. 33A-33C may be arranged to facilitate steering of current and recording of potentials in the vicinity of a single therapeutic target. Embodiments with two sets of stimulating electrodes can be positioned to treat a therapeutic target and steer the current by selecting which electrodes around the lead to energize, as well as whether to energize electrodes from either set of the electrodes, or to energize both electrodes from both sets in coordination.

FIGS. 34A-34C and FIGS. 35A-35C illustrate embodiments of the invention which include internally connected electrodes circumscribing a medical lead, with a plurality of recording electrodes disposed at the axial position of the internal connection. With such embodiments of the invention, independent recordings may be obtained from different angular positions about the lead, at a common axial position near the axial center of the stimulation field.

FIGS. 34A-34C illustrate an embodiment in which three electrodes 135a, 135b and 135c, together with interposed insulating regions, circumscribe the lead. Recording electrodes 140a, 140b, 140c, 140d, 140e, and 140f overlay the internal connections between the stimulating electrodes. Each stimulating electrode 135a-c communicates with an individual electrical conductor 50. Each recording electrode 140a-f communicates with an individual electrical conductor 60.

Figure 35A:
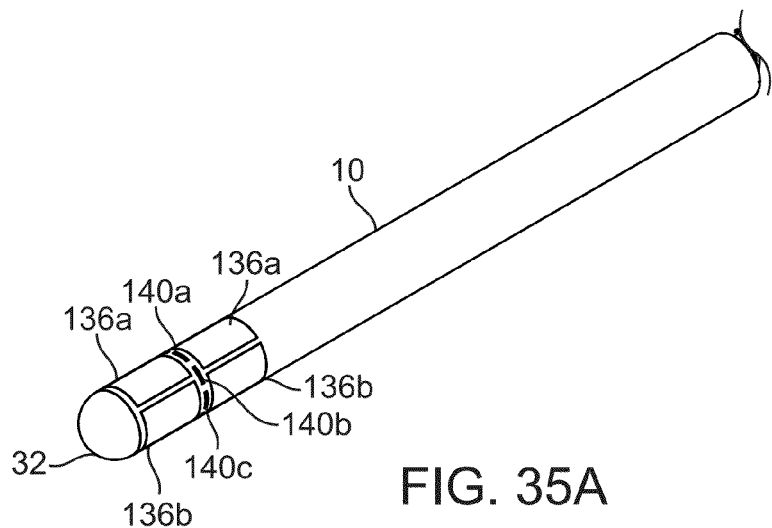
FIGS. 35A-35C illustrate still another embodiment of stimulating and recording structures.
Figure 35B:
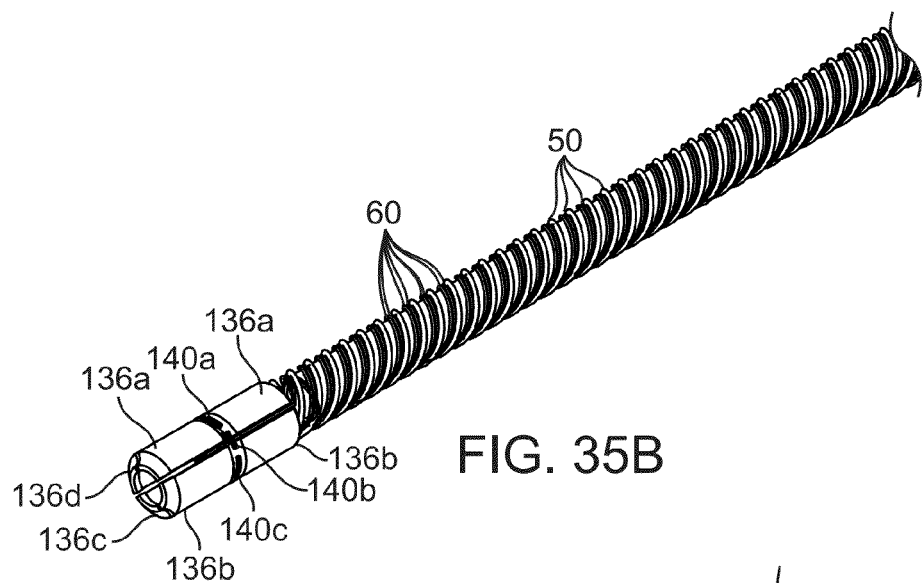
Figure 35C:
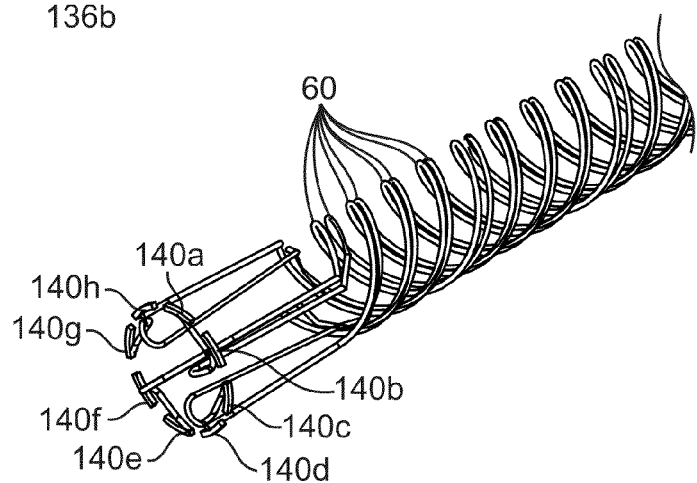

FIGS. 35A-35C illustrate an embodiment in which four electrodes 136a, 136b, 136c and 136d, together with interposed insulating regions, circumscribe the lead. Each of the electrodes has a proximal annular portion, and a distal annular portion that are electrically coupled together with a connector. Recording electrodes 140a, 140b, 140c, 140d, 140e, 140f, 140g and 140h overlay the internal connections between the stimulating electrodes. Each stimulating electrode 136a-d communicates with an individual electrical conductor 50. Each recording electrode 140a-h communicates with an individual electrical conductor 60.

Although the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. A device for stimulating or modulating tissue, said device comprising:
   an elongate member having a longitudinal axis, a proximal end, and a distal end;
   a first pair of adjacent annular stimulating regions, the first pair of annular stimulating regions comprising a proximal annular stimulating region disposed near the distal end of the elongate member, and a distal annular stimulating region disposed near the distal end of the elongate member, the distal annular stimulating region closer to the distal end of the elongate member than the proximal annular stimulating region,
   wherein the proximal annular stimulating region comprises a plurality of independently energizable electrodes adapted to deliver current into the tissue, with adjacent electrodes in the proximal annular stimulating region separated from one another by an insulating member disposed on the elongate member, the proximal annular stimulating region circumscribing the elongate member, and
   wherein the distal annular stimulating region comprises a plurality of independently energizable electrodes adapted to deliver current into the tissue, with adjacent electrodes in the distal annular stimulating region separated from one another by an insulating member disposed on the elongate member, the distal annular stimulating region circumscribing the elongate member, and
   wherein the distal annular stimulating region is axially separated along the longitudinal axis from the proximal annular stimulating member by a gap; and
   a first internal electrical connector entirely disposed near the distal end of the elongate member and electrically coupling a first electrode in the proximal annular stimulating region with a first electrode in the distal annular stimulating region, wherein the first internal electrical connector extends across the gap between the proximal and distal annular stimulating regions.

2. The device of claim 1, wherein the first electrode in the distal annular stimulating region, the first internal electrical connector, and the first electrode in the proximal annular stimulating region form a unitary metal piece.

3. The device of claim 2, wherein the unitary metal piece comprises at least one indentation, relative to the first electrode in the distal annular stimulating region and the first electrode in the proximal annular stimulating region, corresponding to the first internal electrical connector.

4. The device of claim 3, wherein the unitary metal piece comprises a terminal indentation at at least one end of the metal piece.

5. The device of claim 1, further comprising:
   a second internal electrical connector entirely disposed near the distal end of the elongate member and electrically coupling a second electrode in the proximal annular stimulating region with a second electrode in the distal annular stimulating region, wherein the second internal electrical connector extends across the gap between the proximal and distal annular stimulating regions.

6. The device of claim 5, further comprising:
a third internal electrical connector entirely disposed near the distal end of the elongate member and electrically coupling a third electrode in the proximal annular stimulating region with a third electrode in the distal annular stimulating region, wherein the third internal electrical connector extends across the gap between the proximal and distal annular stimulating regions.

7. The device of claim 1, wherein the proximal annular stimulating region completely circumscribes the elongate member.

8. The device of claim 1, further comprising a recording electrode disposed in the gap between the proximal and distal annular stimulating, regions, the recording electrode configured and arranged to record local tissue potentials from the tissue.

9. The device of claim 8, wherein the recording electrode comprises an annular recording electrode completely circumscribing the elongate member.

10. The device of claim 8, wherein the first internal electrical connector comprises a recessed region, and wherein the recording electrode is disposed over the recessed region.

11. The device of claim 1, further comprising a plurality of recording electrodes disposed in the gap between the proximal and distal annular stimulating regions, the recording electrodes configured and arranged to record local tissue potentials from the tissue.

12. The device of claim 1 further comprising a multiple contact connector disposed near the proximal end of the elongate member and electrically coupled with the annular stimulating regions.

13. The device of claim 1, wherein the proximal annular stimulating region consists of four electrodes, with adjacent electrodes separated from one another by an insulating member on the elongate member, the four electrodes disposed circumferentially around the elongate member.

14. The device of claim 1, wherein the proximal annular stimulating region consists of three electrodes, with adjacent electrodes separated from one another by an insulating member on the elongate member, the three electrodes disposed circumferentially around the elongate member.

15. The device of claim 1, further comprising
a second pair of adjacent annular stimulating regions, the second pair of annular stimulating regions adjacent, and distal to, the first pair and comprising a proximal annular stimulating region disposed near the distal end of the elongate member, and a distal annular stimulating region disposed near the distal end of the elongate member, the distal annular stimulating region closer to the distal end of the elongate member than the proximal annular stimulating region,
wherein the proximal annular stimulating region in the second pair comprises a plurality of electrodes configured and arranged to deliver current into the tissue, with adjacent electrodes separated from one another by an insulating member disposed on the elongate member, the proximal annular stimulating region in the second pair circumscribing the elongate member, and
wherein the distal annular stimulating region in the second pair comprises a plurality of electrodes configured and arranged to deliver current into the tissue, with adjacent electrodes separated from one another by an insulating member disposed on the elongate member, the distal annular stimulating region in the second pair circumscribing the elongate member, and wherein the distal annular stimulating region in the second pair is axially separated along the longitudinal axis from the proximal annular stimulating member in the second pair by a second gap;
a second internal electrical connector entirely disposed near the distal end of the elongate member and electrically coupling a first electrode in the proximal annular stimulating region of the second pair with a first electrode in the distal annular stimulating region of the second pair, wherein the second internal electrical connector extends across the second gap between the proximal and distal annular stimulating regions of the second pair.

16. The device of claim 15, further comprising a third internal electrical connector entirely disposed near the distal end of the elongate member and electrically coupling the first electrode in the distal annular stimulating region of the first pair with the first electrode in the proximal annular stimulating region of the second pair, wherein the third internal electrical connector extends across a gap between the distal annular stimulating region of the first pair and the proximal annular stimulating region of the second pair.

17. The device of claim 15, further comprising a second recording electrode disposed in the second gap between the proximal and distal annular stimulating regions of the second pair, the second recording electrode configured and arranged to record local tissue potentials from the tissue.

18. The device of claim 17, wherein the second recording electrode comprises an annular recording electrode completely circumscribing the elongate member.

19. A system for stimulating tissue, comprising:
the device for stimulating or modulating tissue as in claim 1; and
an implantable pulse generator operatively coupleable with the device for stimulating or modulating tissue.

20. The system of claim 19, further comprising an anchoring device configured and arranged to removably couple the device to a patient's head.

* * * * *